United States Patent [19]

McAtee et al.

[11] Patent Number: 6,153,208
[45] Date of Patent: *Nov. 28, 2000

[54] CLEANSING AND CONDITIONING ARTICLE FOR SKIN OR HAIR

[75] Inventors: David Michael McAtee, Mason; Nicholas James Nissing, Cincinnati; Erik John Hasenoehrl, Loveland; David William Cabell, Cincinnati, all of Ohio

[73] Assignee: The Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/152,034

[22] Filed: Sep. 11, 1998

Related U.S. Application Data

[60] Provisional application No. 60/058,608, Sep. 12, 1997, provisional application No. 60/072,440, Jan. 26, 1998, and provisional application No. 60/085,495, May 14, 1998.

[51] Int. Cl.$^7$ .............................. A01N 25/34; A61K 7/42; A61K 7/06; A61K 7/075; A61K 9/70
[52] U.S. Cl. ........................... 424/402; 424/59; 424/70.8; 424/709; 424/70.19; 424/70.21; 424/70.22; 424/70.31; 424/401; 424/404; 424/443; 510/130; 510/135; 510/136; 510/137
[58] Field of Search ..................................... 424/401, 402, 424/59, 404, 443, 70.8, 70.9, 70.19, 70.21, 70.22, 70.31; 510/130, 135, 136, 137

[56] References Cited

U.S. PATENT DOCUMENTS

| | | | |
|---|---|---|---|
| 2,877,115 | 3/1959 | Wemyss, Jr. et al. | 162/179 |
| 2,944,931 | 7/1960 | Yang | 162/179 |
| 3,305,392 | 2/1967 | Britt | 117/154 |
| 3,451,758 | 6/1969 | McClain | 401/201 |
| 3,580,853 | 5/1971 | Parran | 252/152 |
| 3,632,396 | 1/1972 | Perez-Zamora | 117/76 P |
| 3,686,025 | 8/1972 | Morton | 117/140 R |
| 3,795,624 | 3/1974 | Feinstone | 252/91 |
| 3,895,128 | 7/1975 | Gaiser | 428/43 |
| 3,896,807 | 7/1975 | Buchalter | 128/261 |
| 3,944,694 | 3/1976 | McQueary | 428/131 |
| 3,949,137 | 4/1976 | Akrongold et al. | 428/311 |
| 3,956,551 | 5/1976 | Richards | 428/88 |
| 4,145,302 | 3/1979 | Doan | 252/91 |
| 4,206,195 | 6/1980 | Bolich, Jr. et al. | 424/16 |
| 4,206,196 | 6/1980 | Davis | 424/16 |
| 4,303,543 | 12/1981 | Mansy | 132/200 |
| 4,559,157 | 12/1985 | Smith et al. | 252/90 |
| 4,574,052 | 3/1986 | Gupte et al. | 252/90 |
| 4,690,821 | 9/1987 | Smith et al. | 424/401 |
| 4,725,657 | 2/1988 | Shibanai | 523/210 |
| 4,788,060 | 11/1988 | Endicott et al. | 424/443 |
| 4,803,195 | 2/1989 | Holzner | 512/4 |
| 4,806,572 | 2/1989 | Kellett | 521/112 |
| 4,856,541 | 8/1989 | Kellett et al. | 132/110 |
| 4,882,221 | 11/1989 | Bogart et al. | 428/308.8 |
| 4,891,227 | 1/1990 | Thaman et al. | 424/443 |
| 4,891,228 | 1/1990 | Thaman et al. | 424/443 |
| 4,904,524 | 2/1990 | Yoh | 428/311.3 |
| 4,946,617 | 8/1990 | Sheridan et al. | 252/91 |
| 4,948,585 | 8/1990 | Schlein | 424/404 |
| 5,017,365 | 5/1991 | Niedbala | 424/59 |
| 5,063,062 | 11/1991 | Greenspan et al. | 424/443 |
| 5,112,612 | 5/1992 | Garvey et al. | 424/400 |
| 5,139,687 | 8/1992 | Borgher, Sr. et al. | 252/8.6 |

(List continued on next page.)

FOREIGN PATENT DOCUMENTS

| | | |
|---|---|---|
| 1050066 | 3/1991 | China . |
| 1102211 | 5/1995 | China . |
| 1106704 | 8/1995 | China . |
| 1135320 | 11/1996 | China . |
| 0613675A1 | 9/1979 | European Pat. Off. . |
| 186208 | 7/1986 | European Pat. Off. . |
| 0353013A2 | 1/1990 | European Pat. Off. . |
| 0615720A1 | 9/1994 | European Pat. Off. . |
| 0550067B1 | 9/1996 | European Pat. Off. . |
| 58-112542 | 7/1983 | Japan . |
| 63-097699 | 4/1988 | Japan . |
| 1-246478 | 10/1989 | Japan . |
| 6-282290 | 6/1996 | Japan . |
| 9-151400 | 6/1997 | Japan . |
| 9-216809 | 8/1997 | Japan . |
| 1577926 | 10/1980 | United Kingdom . |
| 2163947 | 3/1986 | United Kingdom . |
| 2218430 | 11/1989 | United Kingdom . |
| 2297490 | 8/1996 | United Kingdom . |

(List continued on next page.)

OTHER PUBLICATIONS

Buf–Puf Singles Skin Conditioning, labeling, copyright 1991.
Buf–Puf Singles Oil–Free, labeling, copyright 1991.
Buf–Puf Singles With Cleanser for Normal to Dry Skin, labeling, copyright 1996.
Buf–Puf Singles With Cleanser for Normal to Oily Skin, labeling, copyright 1995.
Tender Bath, Westgate Laboratories, Edison, NJ, 1987. (Product Description—product believed to have been test marketed in Sep., 1986).

Primary Examiner—Shelley A. Dodson
Assistant Examiner—Marina Lamm
Attorney, Agent, or Firm—George W. Allen; Fumiko Tsuneki

[57] ABSTRACT

The present invention relates to a substantially dry, disposable, personal cleansing article useful for both cleansing the skin or hair, and more particularly to a disposable, cleansing article having a substrate which preferably comprises of multiple layers. These articles are used by the consumer by wetting the dry article with water. The article comprises a water insoluble substrate having at least a first portion that is wet extensible and at least a second portion that is less wet extensible than said first portion and a lathering surfactant. Preferably, the articles of the present invention further comprise a conditioning component.

27 Claims, 4 Drawing Sheets

U.S. PATENT DOCUMENTS

| | | | |
|---|---|---|---|
| 5,185,155 | 2/1993 | Behan et al. | 424/451 |
| 5,232,613 | 8/1993 | Bacon et al. | 252/8.6 |
| 5,236,615 | 8/1993 | Trinh et al. | 252/174.11 |
| 5,246,611 | 9/1993 | Trinh | 252/8.6 |
| 5,292,533 | 3/1994 | McMahon et al. | 242/408 |
| 5,348,667 | 9/1994 | Bacon et al. | 252/8.6 |
| 5,376,287 | 12/1994 | Borcher, Sr. et al. | 252/8.8 |
| 5,466,460 | 11/1995 | McMahon et al. | 424/408 |
| 5,538,732 | 7/1996 | Smith et al. | 424/402 |
| 5,552,378 | 9/1996 | Trinh et al. | 512/3 |
| 5,605,749 | 2/1997 | Pike et al. | 442/60 |
| 5,620,694 | 4/1997 | Girardot | 424/402 |
| 5,648,083 | 7/1997 | Blieszner et al. | 424/402 |
| 5,661,170 | 8/1997 | Chodosh | 514/390 |
| 5,683,971 | 11/1997 | Rose et al. | 510/130 |
| 5,698,475 | 12/1997 | Vlasblom | 442/59 |
| 5,702,992 | 12/1997 | Martin et al. | 442/123 |
| 5,871,762 | 2/1999 | Venkitaraman et al. | 424/402 |

FOREIGN PATENT DOCUMENTS

| | | |
|---|---|---|
| WO 89/03639 | 5/1989 | WIPO . |
| WO 93/05141 | 3/1993 | WIPO . |
| WO 93/21899 | 11/1993 | WIPO . |
| WO 94/27569 | 12/1994 | WIPO . |
| WO 95/00116 | 1/1995 | WIPO . |
| WO 95/16824 | 6/1995 | WIPO . |
| WO 95/31189 | 11/1995 | WIPO . |
| WO 96/04937 | 2/1996 | WIPO . |
| WO 96/06595 | 3/1996 | WIPO . |
| WO 96/14835 | 5/1996 | WIPO . |
| WO 96/24329 | 8/1996 | WIPO . |
| WO 96/24723 | 8/1996 | WIPO . |
| WO 96/34035 | 10/1996 | WIPO . |
| WO 96/36315 | 11/1996 | WIPO . |
| WO 97/00001 | 1/1997 | WIPO . |
| WO 97/07781 | 3/1997 | WIPO . |
| WO 97/16066 | 5/1997 | WIPO . |
| WO 97/45256 | 12/1997 | WIPO . |

CLEANSING AND CONDITIONING ARTICLE FOR SKIN OR HAIR

CROSS-REFERENCE TO RELATED APPLICATIONS

This application claims the benefit under 35 USC §119(e) of the U.S. provisional application of David Michael McAtee, Nicholas James Nissing, and Erik John Hasenoehrl having Ser. No. 60/058,608, filed Sep. 12, 1997; the U.S. provisional application of David Michael McAtee, Nicholas James Nissing, Erik John Hasenoehrl, and David William Cabell having Ser. No. 60/072,440, filed Jan. 26, 1998; and the U.S. provisional application of David Michael McAtee, Nicholas James Nissing, Erik John Hasenoehrl, and David William Cabell having Ser. No. 60/085,495, filed May 14, 1998.

TECHNICAL FIELD

The present invention relates to a substantially dry, disposable, personal cleansing article useful for both cleansing and conditioning the skin or hair, and more particularly to a disposable, cleansing, and conditioning article having a substrate which preferably comprises of multiple layers. These articles are used by the consumer by wetting the dry article with water. The article comprises a water insoluble substrate having at least a first portion that is wet extensible and at least a second portion that is less wet extensible than said first portion and a lathering surfactant. Preferably, the articles of the present invention further comprise a conditioning component.

Use of the substrate enhances lathering at low surfactant levels, increases cleansing and exfoliation, optimizes delivery and deposition of conditioning ingredients, and provides desirable characteristics such as texture, thickness and bulk. As a result, this invention provides effective cleansing using low, and hence less irritating, levels of surfactant while providing superior conditioning benefits by using a substrate having desirable characteristics.

The invention also encompasses articles comprising various active ingredients for delivery to the skin or hair.

The invention also encompasses a method for consistent deposition of conditioning agents to the skin or hair.

The invention also encompasses a method for cleansing and moisturizing the skin or hair using the articles of the present invention and also to methods for manufacturing these articles.

BACKGROUND OF THE INVENTION

Personal cleansing articles have traditionally been marketed in a variety of forms such as bar soaps, creams, lotions, and gels. These cleansing formulations have attempted to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and not leave the skin or hair overly dry after frequent use.

However, these traditional forms of personal cleansing articles have the inherent problem of balancing cleansing efficacy against delivering a conditioning benefit. One solution to this problem is to use separate cleansing and conditioning articles. However, this is not always convenient or practical and many consumers would prefer to use a single article which can both cleanse and condition the skin or hair. In a typical cleansing composition the conditioning ingredients are difficult to formulate because many conditioners are incompatible with the surfactants, resulting in an undesirable non-homogenous mixture. To obtain a homogeneous mixture with conditioning ingredients, and to prevent the loss of conditioning ingredients before deposition, additional ingredients, e.g. emulsifiers, thickeners, and gellants are often added to suspend the conditioning ingredients within the surfactant mixture. This results in an aesthetically pleasing homogenous mixture, but often results in poor deposition of conditioning ingredients, because the conditioners are emulsified and not efficiently released during cleansing. Also, many conditioning agents have the disadvantage of suppressing lather generation. Lather suppression is a problem because many consumers seek cleansing articles that provide a rich, creamy, and generous lather.

Therefore, it is seen that conventional cleansing articles which attempt to combine surfactants and conditioning ingredients suffer from disadvantages inherently resulting from the incompatibilities of surfactants and conditioners. A need clearly exists to develop cleansing systems which provide effective cleansing and yet consistently provide sufficient conditioning in a single article.

It is also highly desirable to deliver cleansing and conditioning benefits from a disposable, single use article. Disposable articles are convenient because they obviate the need to carry cumbersome bottles, bars, jars, tubes, and other forms of both cleansing and conditioning articles. Disposable articles are also a more sanitary alternative to the use of a sponge, washcloth, or other cleansing implement intended for multiple reuse, because such implements develop bacterial growth, unpleasant odors, and other undesirable characteristics related to repeated use.

In addition, consumer habits of using disposable articles having two surfaces vary considerably. When preparing to use such articles, consumers will generally wet the article and then "lather" it before contacting the article with their skin or hair. "Lathering" is achieved by rubbing the surfaces of the article on or against each other prior to use of the article. If the surface containing the conditioning agents is first used in lathering and the same surface is then used to contact the skin or hair, deposition of the conditioning agents is considerably decreased due to emulsification of the conditioning agents by the surfactant. If, however, the surface not containing the conditioning agents (e.g., a surfactant-containing surface) is rubbed together to produce the lather and the surface containing the conditioning agents is then used to contact the skin or hair, maximum deposition of conditioning agents is achieved. If both surfaces of the article are treated with the conditioning agents, the same inconsistent deposition can result. Maximum deposition of conditioning agents would result only if a non-lathered surface containing conditioning agents is contacted with the skin or hair.

It has been surprisingly found that if the conditioning component (the combination of the conditioning agents) has a minimum lipid hardness value of 0.02 kg., this inconsistent deposition of conditioning agents is considerably diminished. It is believed that increasing conditioning component hardness decreases transfer within the substrate and also decreases emulsification of the conditioning agents by the surfactants during the lathering step. As a result, more of the conditioning agents remain available for mechanical transfer via contact with the skin or hair.

It is also highly desirable to provide a cleansing and conditioning article having the qualities of a washcloth. These desirable features can be realized in disposable articles by providing proper texture, thickness (caliper), and bulk (volume per unit weight). A relatively high value of texture is desirable for aiding in cleansing of skin and hair. Relatively high values of caliper and bulk are desirable for providing volume in the article for receiving and containing liquids. Typically, such washcloth-like articles have a substrate which includes one or more materials or layers. The substrate can be pre-moistened with a wetting agent prior to use, or alternatively, can be combined with a liquid at the point of use of the article. Pre-moistened wiping articles are also referred to as "wet wipes" and "towelettes."

One method of imparting texture and bulk to a washcloth-like article is by combining layers of plies having different properties. U.S. Pat. No. 4,469,735 issued Sep. 4, 1984 to Trokhan discloses a multiple ply tissue paper article having a wet microcontracted constraining paper ply and a dry creped constrained paper ply. Portions of the constrained ply are adhered to the constraining ply. When the multiple ply article is wetted, unadhered portions of the constrained ply pucker in the Z-direction to provide texture and bulk.

While the structure in U.S. Pat. No. 4,469,735 provides the advantage of texture and bulk upon wetting, it requires the use of wet microcontraction procedures on a paper machine in order to prepare such structures. Further, the structures in the '735 patent have reported wet calipers (thickness) which are lower than the corresponding dry calipers.

It has been surprisingly found in the present invention that articles can be developed to provide effective cleansing and consistent conditioning in a convenient, inexpensive, and sanitary disposable personal cleansing article having the desirable properties of a washcloth. The present invention provides the convenience of not needing to use both a separate cleansing and conditioning article. The present invention is highly convenient to use because it is in the form of a substantially dry article that is wetted before use.

The present invention relates to a dry, disposable, personal cleansing article useful for both cleansing and conditioning the skin or hair. These articles are used by the consumer by wetting the dry article with water. The article consists of a water insoluble substrate having at least a portion that is wet extensible, a lathering surfactant, and preferably a conditioning component having a lipid hardness value of at least 0.02 kg. Without being limited by theory, it is believed that the substrate enhances lathering at low surfactant levels, increases cleansing and exfoliation, and optimizes delivery and consistent deposition of the conditioning ingredients. It is also believed that having a conditioning component lipid hardness value of at least 0.02 kg. provides greater efficient and consistent deposition of conditioning agents to the skin or hair. As a result, this invention provides effective cleansing using low, and hence less irritating, levels of surfactant while providing superior conditioning benefits in a consistent and efficient manner. It has also been found that these articles are useful for delivering a wide range of active ingredients to the skin or hair during the cleansing process.

Accordingly, it is an object of the present invention to provide substantially dry washcloth-like articles for both cleansing conditioning the skin or hair wherein the articles are used in combination with water.

It is another object of the present invention to provide articles comprising a water insoluble substrate, a surfactant, and a conditioning component having a lipid hardness value of at least 0.02 kg.

It is another object of the present invention to provide articles which are disposable and intended for single use.

It is another object of the present invention to provide articles which are mild to the skin or hair.

It is another object of the present invention to provide articles which, upon wetting, are capable of generating an Average Lather Volume of greater than or equal to about 30 ml.

It is another object of the present invention to provide articles useful for delivering active ingredients to the skin or hair during the cleansing and conditioning process.

It is another object of the present invention to provide articles which consistently deposit the conditioning component and other active ingredients onto the skin or hair.

It is another object of the present invention to provide methods of cleansing and consistently conditioning the skin or hair.

It is another object of the present invention to provide methods of consistently providing deposition of the conditioning agents and other active ingredients.

It is another object of the present invention to provide methods of manufacturing the articles of the present invention.

It is another an object of the present invention to provide a disposable cleansing and conditioning articles which exhibits increased texture and bulk upon wetting.

Another object of the present invention is to provide a disposable cleansing and conditioning article having a wet caliper greater than the dry caliper of the article.

Another object of the present invention is to provide a disposable cleansing and conditioning article having an apertured paper layer which is foreshortened, and which provides increased texture and bulk upon wetting.

These and other objects of this invention will become apparent in light of the following disclosure.

SUMMARY OF THE INVENTION

The present invention relates to a disposable, single use personal care cleansing and conditioning article comprising: (A) a water insoluble substrate, wherein at least a first portion of said substrate is wet extensible and at least a second portion of said substrate is less wet extensible than said first portion, and (B) at least one lathering surfactant added onto or impregnated into the substrate. The article is substantially dry prior to use. Preferred embodiments of the present invention are capable of generating an Average Lather Volume of greater than or equal to about 30 ml upon wetting.

In further embodiments, the present invention further comprises a conditioning component added onto or impregnated into the substrate. The conditioning component preferably has a lipid hardness value of greater than about 0.02 kg.

In still further embodiments, the present invention relates to disposable, single use personal care cleansing and conditioning article comprising:
  (A) a water insoluble substrate, wherein at least a first portion of said substrate is wet extensible and at least a second portion of said substrate is less wet extensible than said first portion, and
  (B) a cleansing and conditioning composition added onto or impregnated into the substrate comprising:
    (i) at least one lathering surfactant, and
    (ii) a conditioning component having a lipid hardness value of greater than about 0.02 kg.
In this embodiment the lathering surfactant and the conditioning component are separately or simultaneously added onto or impregnated into the water insoluble substrate. In such an embodiment, the article is also substantially dry prior to use, and is preferably capable of generating the above-described Average Lather Volume upon wetting.

In still further embodiments, the present invention provides a multiple layer disposable cleansing and conditioning article. The wiping article includes at least two layers, or plies. The first layer is extensible when it is wetted and is preferably apertured. The second layer is less wet extensible when wetted than the first layer. Selected portions of the first layer are joined to the second layer to inhibit wet extension of the first layer in the plane of the first layer.

When the first layer is wetted, the second layer constrains extension of the first layer in the plane of the first layer. As a result, portions of the first layer deform, such as by buckling or puckering, in the Z-direction (perpendicular to the plane of the first layer).

The first layer preferably has a wet extensibility of at least about 4 percent, more preferably at least about 10 percent, and still more preferably at least about 20 percent as measured using the "Wet Extensibility Test" provided hereinafter. The first layer can be foreshortened to provide the desired wet extensibility. In one embodiment, the first layer comprises a wet laid, apertured paper web which is foreshortened about 30 percent by dry creping.

The second layer has a wet extensibility that is less than that of the first layer. The wet extensibility of the first layer minus the wet extensibility of the second layer is preferably at least about 4 percent, more preferably at least about 10 percent, and still more preferably at least about 20 percent. The second layer can comprise a nonwoven web of natural fibers, synthetic fibers, or combinations thereof. In one embodiment, the second layer comprises a hydroentangled nonwoven web of rayon and polyester fibers.

The disposable cleansing and conditioning article can have a wet caliper to dry caliper ratio greater than 1.0, more preferably at least about 1.1, even more preferably at least about 1.2, and most preferably at least about 1.4, where the wet to dry caliper ratio is a relative measure of the wet and dry thickness of the cleansing and conditioning article. The wet to dry caliper ratio is measured according to the procedure set forth hereinafter.

Preferably, selected portions of the first layer are joined to the second layer in a predetermined bonding pattern to provide a plurality of unbonded regions between the layers. In one embodiment, the first and second layers are bonded together using a hot melt adhesive.

In still further embodiments, the present invention relates to a method of manufacturing a disposable, single use personal care cleansing and conditioning article comprising the step of separately or simultaneously adding onto or impregnating into a water insoluble substrate having at least a portion that is wet extensible (A) at least one lathering surfactant, and
(B) a conditioning component having a lipid hardness value of greater than about 0.02 kg.

The resulting article is substantially dry, and is preferably capable of generating the above-described Average Lather Volume upon wetting.

In still further embodiments, the present invention relates to methods for cleansing and conditioning the skin or hair with the personal cleansing articles described herein.

In even further embodiments, the present invention relates to methods of consistently depositing conditioning agents to the skin or hair.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

DETAILED DESCRIPTION OF THE INVENTION

Figure 1:
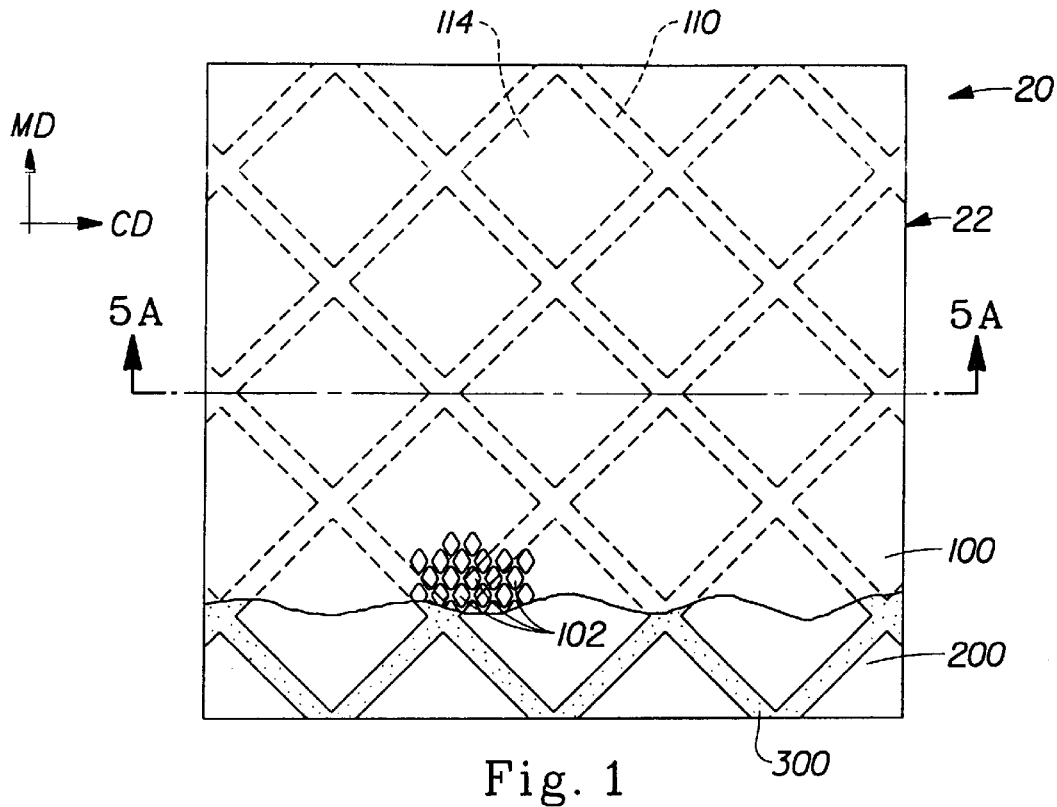
FIG. 1 is a plan view illustration of one embodiment of a cleansing and conditioning article of the present invention, the article including an extensible first layer and a less extensible second layer, with the first layer shown facing the viewer, and with a portion of the first layer shown cut away to show a continuous network of generally parallel sets of intersecting lines of adhesive which serve to bond the first layer to the second layer, the bonded region defining generally diamond-shaped unbonded regions.

The personal cleansing articles of the present invention are highly efficacious for cleansing the skin or hair while at the same time providing effective deposition of conditioning agents. The articles can also contain other non-conditioning active ingredients to be deposited onto the skin or hair.

Without being limited by theory it is believed that the substrate significantly contributes to generation of lather and deposition of conditioning agents and any other active ingredients. It is believed that this increase in lathering and deposition is the result of the surface action of the substrate. As a result, milder and significantly lower amounts of surfactants may be employed. The decreased amount of required surfactant is believed to relate to the decrease in the drying effect of the skin or hair by the surfactants. Furthermore, the diminished amount of surfactant dramatically lowers the inhibitory action (e.g., via emulsification or direct removal by the surfactants) which surfactants exhibit regarding deposition of conditioning agents.

Without being limited by theory, the substrate also enhances deposition of conditioning agents and active ingredients. Since the invention is in dry form, the invention does not require emulsifiers, which can inhibit deposition of conditioning agents and active ingredients. Furthermore, because the skin conditioners and active ingredients are dried onto or impregnated into the substrate, they are transferred directly to the skin or hair by surface contact of the wetted article to the skin.

The substrate also enhances cleansing. The substrate can have differing textures on each side, e.g. a rough side and a smooth side. The substrate acts as an efficient lathering and exfoliating implement. By physically coming into contact with the skin or hair, the substrate significantly aids in cleansing and removal of dirt, makeup, dead skin, and other debris.

Finally, a substrate having at least a portion that is wet extensible provides the desired qualities (e.g., proper texture, thickness, and bulk) of a washcloth. It is also believed that these particular types of substrates enhance lather generation.

It is also believed that having a minimum lipid hardness value of 0.02 kg. for the conditioning component provides consistent deposition of the conditioning agents to the skin or hair by decreasing transfer within the substrate and also decreasing emulsification of the conditioning agents by the surfactants during the lathering step.

By a "lathering surfactant" is meant a surfactant, which when combined with water and mechanically agitated generates a foam or lather. Preferably, these surfactants should be mild, which means that these surfactants provide sufficient cleansing or detersive benefits but do not overly dry the skin or hair (e.g., removing too much natural oil and/or moisture), and yet meet the lathering criteria described above.

The term "lathering product" or "lathering article," as used herein, means that the product or article contains enough of the surfactants described herein to generate $\geq 30$ ml of Lather Volume, as described herein in the Lather Volume Test. These Lather Volume measurements are conducted with a medium hardness water (8–10 grains per gallon) at 95° C.

The terms "disposable" or "single use", are used herein in their ordinary sense to mean a article that is disposed or discarded after one usage event.

The term "conditioning component," as used herein, means a combination of the conditioning agents. This combination can also include lipid hardening materials.

The term "water-activated," as used herein, means that the present invention is presented to the consumer in dry form to be used after it is wetted with water. It is found that these articles produce a lather or are "activated" by contacting them with water and then further subjecting the article to mechanical forces, such as rubbing.

The term "substantially dry," as used herein, means that prior to use the article is substantially free of water and generally feels dry to the touch. Thus, the articles of the present invention will generally comprise less than about 10% by weight of water, preferably less than about 5% by weight of water, and more preferably less than about 1% by weight of water, the forgoing measured in a dry environment, e.g., low humidity. One of ordinary skill in the art would recognize that the water content of a article such as in the present invention can vary with the relative humidity of the environment.

The term "mild" as used herein in reference to the lathering surfactants and articles of the present invention means that the articles of the present invention demonstrate skin mildness comparable to a mild alkyl glyceryl ether sulfonate (AGS) surfactant based synthetic bar, i.e. synbar. Methods for measuring mildness, or inversely the irritancy, of surfactant containing articles, are based on a skin barrier destruction test. In this test, the milder the surfactant, the lesser the skin barrier is destroyed. Skin barrier destruction is measured by the relative amount of radio-labeled (tritium labeled) water ($3H-H_2O$) which passes from the test solution through the skin epidermis into the physiological buffer contained in the diffusate chamber. This test is described by T. J. Franz in the J. Invest. Dermatol., 1975, 64, pp. 190–195; and in U.S. Pat. No. 4,673,525, to Small et al., issued Jun. 16, 1987, which are both incorporated by reference herein in their entirety. Other testing methodologies for determining surfactant mildness well known to one skilled in the art can also be used.

The term "deposition consistency," as used herein, means that deposition of the conditioning agents comprising the conditioning component will be relatively unvarying no matter how the consumer prepares to use, and the actual uses, the cleansing and conditioning article (e.g., lathering the side of the substrate carrying the conditioning component versus lathering the substrate side with the surfactant). The articles of the present invention will have a deposition consistency of greater than about 60%, preferably greater than about 65%, more preferably greater than about 70%, and most preferably greater than about 75%. The deposition consistency measurement is the quotient obtained by dividing the amount of deposition of conditioning agents that occurs via "non-ideal lathering and use" by the amount of deposition of conditioning agents that occurs via "ideal lathering and use." Non-ideal lathering, as used herein, means that lathering is achieved by rubbing together or against itself the surface of the article containing the conditioning agents and then contacting the skin or hair with the same surface. This causes inefficient deposition of the conditioning agents because some of the conditioning agents become emulsified by the surfactant. Ideal lathering, as used herein, means that lathering is achieved by rubbing together or against itself the surface of the article containing surfactant, but not containing conditioning agents, and then contacting the skin or hair with the surface containing the conditioning component. The same reference points would apply if both surfaces of the substrate are treated with the conditioning agents (e.g. deposition obtained from lathering and contacting the skin with the same lathered surface containing emulsified conditioning agents versus contacting the skin with the non-lathered surface which contains non-emulsified conditioning agents). Deposition consistency is maximized when the lipid hardness value of the conditioning component is greater than about 0.02 kg.

The personal care articles of the present invention comprise the following essential components: (A) a water insoluble substrate, wherein at least a first portion of said substrate is wet extensible and at least a second portion of said substrate is less wet extensible than said first portion, and (B) at least one lathering surfactant added onto or impregnated into the substrate. The articles of the present invention can further comprise a conditioning component added onto or impregnated into the substrate.

Water Insoluble Substrate having at Least a Portion that is Wet Extensible

The articles of the present invention comprise a water insoluble substrate wherein at least a first portion of said substrate is wet extensible and at least a second portion of said substrate is less wet extensible than said first portion. By "water insoluble" is meant that the substrate does not dissolve in or readily break apart upon immersion in water. By wet extensible is meant that the material has a tendency to elongate at least in one direction when wetted. A test for measuring extensibility is provided below. The water insoluble substrate is the implement or vehicle for delivering the lathering surfactant and the conditioning component of the present invention to the skin or hair to be cleansed and conditioned. Without being limited by theory, it is believed that the substrate, as the means for transmitting mechanical forces and providing agitation, provides a lather generating effect and also aids in the deposition of the conditioning component.

Figure 2:
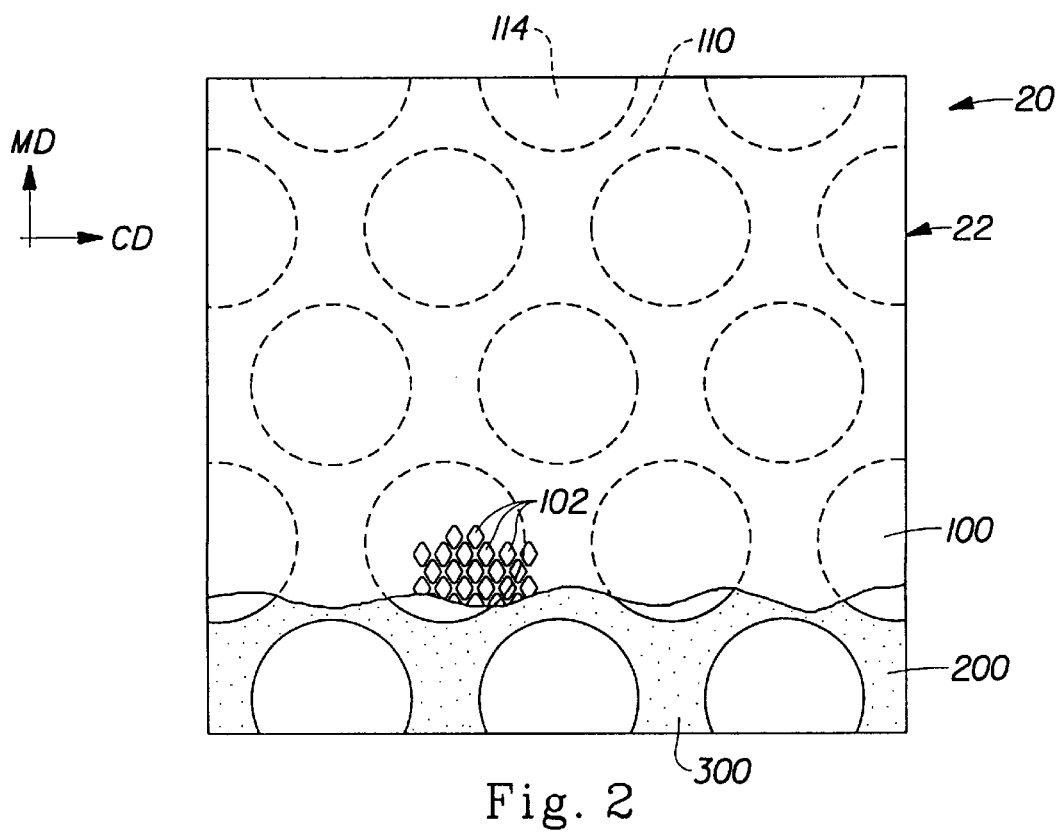
FIG. 2 is an illustration of another embodiment of a cleansing and conditioning article of the present invention, the article including an extensible first layer and a less extensible second layer, with the first layer shown facing the viewer, and with a portion of the first layer shown cut away to show a continuous network of adhesive which serves to bond the first layer to the second layer, the bonded region defining generally circular-shaped unbonded regions.
Figure 3:
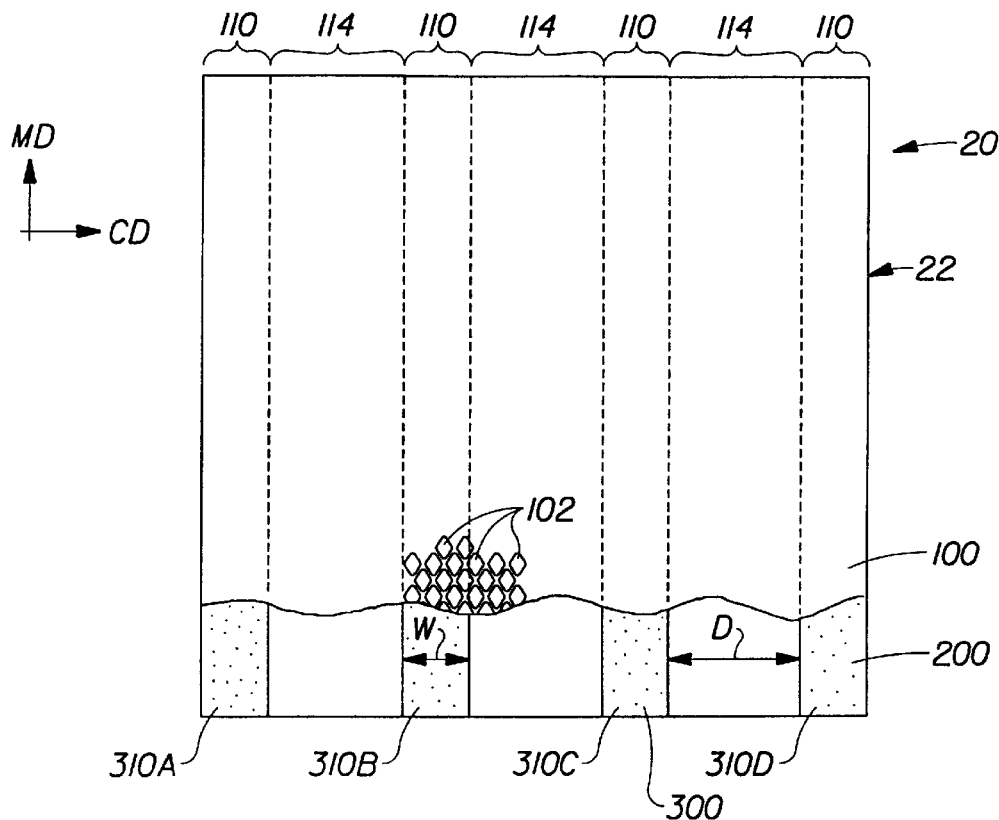
FIG. 3 is a plan view illustration of another embodiment of a cleansing and conditioning article of the present invention, the article including an extensible first layer and a less extensible second layer, with the first layer shown facing the viewer, and with a portion of the apertured layer shown cut away to show generally parallel, spaced apart zones of adhesive extending generally parallel to the machine directions of the apertured layer and the nonwoven layer.

One embodiment of a water insoluble substrate having at least a portion that is wet extensible is illustrated in FIGS. 1–3. In this embodiment, the present invention comprises a multiple layer disposable wiping article 20. FIGS. 1–3 illustrate a two layer, or two ply, embodiment of the present invention. Alternatively, the disposable wiping article can include more than two layers.

The disposable cleansing and conditioning article 20 comprises a substrate designated generally by reference numeral 22. The substrate 22 comprises a first layer 100 and a second layer 200. The first layer 100 is extensible, and in particular is extensible when wetted, e.g., the first layer is wet extensible. By "wet extensible" is meant that a material has a tendency to elongate in at least one direction when wetted. In general, "wetted" refers to wetting with aqueous solutions, such as water, which are capable of inducing extension in the first layer. For example, water relaxes the crepe in foreshortened paper, thereby causing an extension of the paper in at least one direction in the plane of the paper. Without being bound by theory, the relaxation of crepe may be a result of the loss of hydrogen bonds within the paper structure due to the presence of water. However, any fluid, mixture, or solution which could cause this crepe relaxation would be considered to "wet" the article. The second layer 200 is relatively less wet extensible when wetted than the first layer 100. Extensibility is measured according to the "Wet Extensibility Test" described below, and is reported as a percentage.

Selected portions of the first layer 100 are joined, directly or indirectly, to second layer 200 to inhibit wet extension of the first layer in the plane of the first layer. In FIGS. 1 and 2, selected portions of the first layer 100 are joined to the second layer 200 to provide continuous bonded regions designated 110 and discrete unbonded regions 114.

In a preferred embodiment shown in FIG. 1, the bonded regions 110 are shown as a continuous network of intersecting lines forming generally diamond-shaped unbonded regions 114. The width and spacing of the intersecting lines of bonded regions 110, may be adjusted to the desired size and spacing of the diamond-shaped unbonded regions 114. The continuous network of intersecting lines may be virtually any pattern, resulting in unbonded regions of virtually limitless geometric shapes, including, for example, squares, rectangles, and triangles. The network need not be completely continuous, nor limited to a pattern of straight or uniform lines, but may, for example, be a network resulting in circular, oval, or other non-polygonal geometric shapes. An adhesive, such as a hot melt adhesive, designated by reference numeral 300 in FIGS. 1–3, can be used to join the first layer 100 to second layer 200.

When the first layer is wetted, there is a tendency for the first layer 100 to expand along one or more directions in the plane of the first layer. (The plane of the first layer is parallel to the plane of FIG. 1). However, because of the relatively lower wet extensibility of the second layer 200, the second layer constrains extension of the first layer 100 in the plane of the first layer. As a result, the unbonded regions 114 of the first layer 100 deform, such as by buckling or puckering in the Z-direction, perpendicular to the plane of the first layer 100.

Figure 5A:
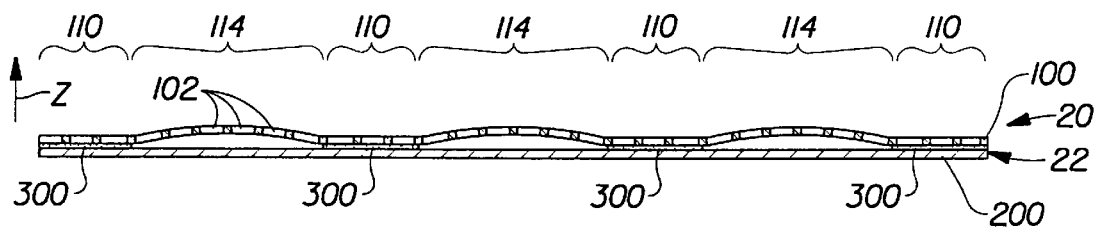
FIG. 5A is a cross-sectional illustration of the cleansing and conditioning article of the present invention taken along the direction indicated by line 5—5 in FIG. 1, and showing the article prior to wetting of the first layer.
Figure 5B:
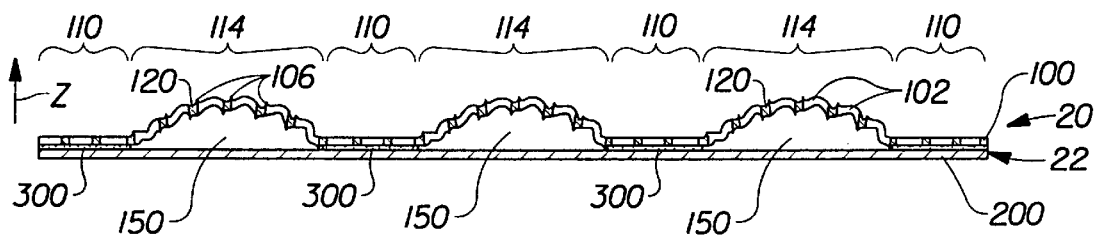
FIG. 5B is a cross-sectional illustration taken along the direction indicated by line 5—5 in FIG. 1, and showing the article after wetting of the first layer.

FIG. 5A is a cross-sectional illustration of the cleansing and conditioning article 20 prior to wetting of the first layer 100. As shown in FIG. 5A, the wiping article is generally flat prior to wetting. FIG. 5B is a cross-sectional illustration similar to that of FIG. 5A, but showing the article 20 after wetting of the first layer 100. FIG. 5B shows out of plane deformation of the first layer 100 upon wetting of the first layer 100. The Z-direction is indicated in FIGS. 5A and 5B. The deformation of the wetted first layer 100 provides the article 20 with elevated ridges 120 which increase the wet texture, wet caliper (thickness) and wet bulk of the article 20. The elevated ridges 120 also provide pockets 150 disposed between the unbonded portions of the first layer 100 and the underlying portions of the second layer. In particular, the article 20 has a wet caliper to dry caliper ratio which is greater than 1.0, preferably at least about 1.1, more preferably at least about 1.2, and most preferably at least about 1.4. The wet caliper to dry caliper ratio is a measure of the thickness of the article 20, when wetted, relative to the thickness of the dry article 20 prior to wetting. The wet caliper to dry caliper ratio is measured according to the procedure "Wet Caliper to Dry Caliper Ratio" provided below.

In a preferred embodiment, as shown in FIG. 1, the first layer 100 is apertured, the first layer 100 comprising a plurality of apertures 102 which extend through the thickness of the first layer 100. Apertures, while not necessary to practice the present invention, add greatly to the desired texture and bulk of wiping article 20. In FIGS. 1–3, apertures 102 are shown on only a portion of the first layer 100 for clarity. When an apertured first layer is used, the deformation of the wetted first layer 100 again provides the article 100 with elevated ridges 120 which increase the wet texture, wet caliper (thickness) and wet bulk of the article 20. However, in this embodiment, the elevated ridges 120 have apertures 102 which provide a flow path through which liquids and/or small particles can enter the pockets 150.

Additionally, since the article 20 is used with, or includes a lathering agent, such as a surfactant, the apertures 102 can aid in the incorporation of air during the lathering process, thereby improving lather generation. For instance, a portion of the article 20 can be coated with or otherwise treated with a surfactant composition, as described more fully below. The article 20 can be wetted with water to activate the surfactant, and the airflow generated through the apertures 102 during use of the article (e.g. washing or wiping) can help to generate lather.

The size and number of the apertures 102 can influence the speed of lather generation and the quality of lather produced. A relatively small number of relatively large apertures 102 will tend to reduce the time required to generate lather, but will yield relatively large lather bubbles with a translucent appearance. On the other hand, a relatively larger number of relatively smaller apertures 102 will tend to reduce bubble size, thereby increasing lather creaminess and opacity, but at the expense of increasing the time required to generate lather. Between about 4 and about 300 apertures per inch can provide suitable lather speed and quality.

Another advantage has been identified when first layer 100 is apertured. As shown in FIG. 5B, in addition to the formation of elevated ridges 120, the wet extension of first layer 100 around apertures 102 forms what can best be described as cusps 106, or surface irregularities formed by the apertures 102. Cusps 106 give added texture to the surface on the side of apertured surface 22 of first layer 100. This added texture may be modified as needed by adjusting the size and spacing of apertures 102.

Also depicted in FIG. 3, is another variation on the configuration of bonded and unbonded regions. In the embodiment shown, the bonded regions 110 are generally parallel, spaced apart regions which extend along substantially the full length of the article 20, and define generally parallel, spaced apart unbonded regions 114 of the first layer 100. In FIG. 3, the unbonded regions 114 extend along substantially the full length of the article 20. An adhesive, designated by reference numeral 300 in FIGS. 1 and 2 and numerals 300, 310A–310D in FIG. 3, can be used to join the first layer 100 to the second layer 200.

In a currently preferred embodiment, a wipe 20 of the present invention comprises an apertured cellulosic paper first layer bonded to a synthetic nonwoven in a continuous network of intersecting lines defining diamond-shaped unbonded regions. This combination of materials and bonding method and pattern provides for a preferred wipe that exhibits increased texture and bulk on one side upon wetting, while maintaining relatively smooth softness on the other side, and has a wet caliper greater than the dry caliper.

In addition to the above description, it has been found that an additional processing step involving heating the substrate after bonding further improves the texture and bulk, as well as the general aesthetic qualities of the wipe. Without being bound by theory, it is believed that the process of heating causes the thermoplastic adhesive to contract, thereby further causing out-of-plane (Z-direction) deformation of the first layer, as well as the second layer. By contracting in the plane of the wipe article, both layers experience a Z-direction increase in caliper, giving increased overall caliper with a pleasing quilted look.

For example, a wipe that has been adhesively bonded with an EVA hot melt adhesive (one suitable adhesive is a hot melt adhesive commercially available as 111382-01 from Ato-Findley Adhesives of Wauwatosa, Wis.), may increase in caliper between 10–20% after a post-lamination heat treatment. In this case, a suitable hot melt adhesive is applied and the resulting article is cooled to room temperature. Heat treatment may then be performed, for example, raising the temperature to 100 degrees Celsius for 20 seconds is sufficient to initiate contraction of the polymer network. While not being bound by theory, it is believed that for this process to be effective, the pattern of bonding must be a continuous or essentially continuous network. Discrete bond sites may not sufficiently contract to improve the appearance of the article.

First Layer:

Referring to the components of the article 20 in more detail, suitable materials from which the first layer 100 can be formed include foreshortened (such as by creping) wetlaid paper webs. Other suitable materials can include woven materials, nonwoven materials, foams, battings, and the like.

The first layer 100 should be constructed to have a wet extensibility of at least 4 percent, more preferably at least about 10 percent, and still more preferably at least about 20 percent. In one embodiment, the first layer has a wet extensibility of at least about 25 percent. Preferably, the difference between the wet extensibility of the first layer and the wet extensibility of the second layer (the wet extensibility of the second layer subtracted from the wet extensibility of the first layer) is at least about 4 percent, more preferably at least about 10 percent, and still more preferably at least about 25 percent.

The fibers or filaments of the first layer 100 can be natural (e.g. cellulosic fibers such as wood pulp fibers, cotton linters, and bagasse fibers) or synthetic (e.g. polyolefins, rayon, polyamides or polyesters), or combinations thereof.

Figure 4:
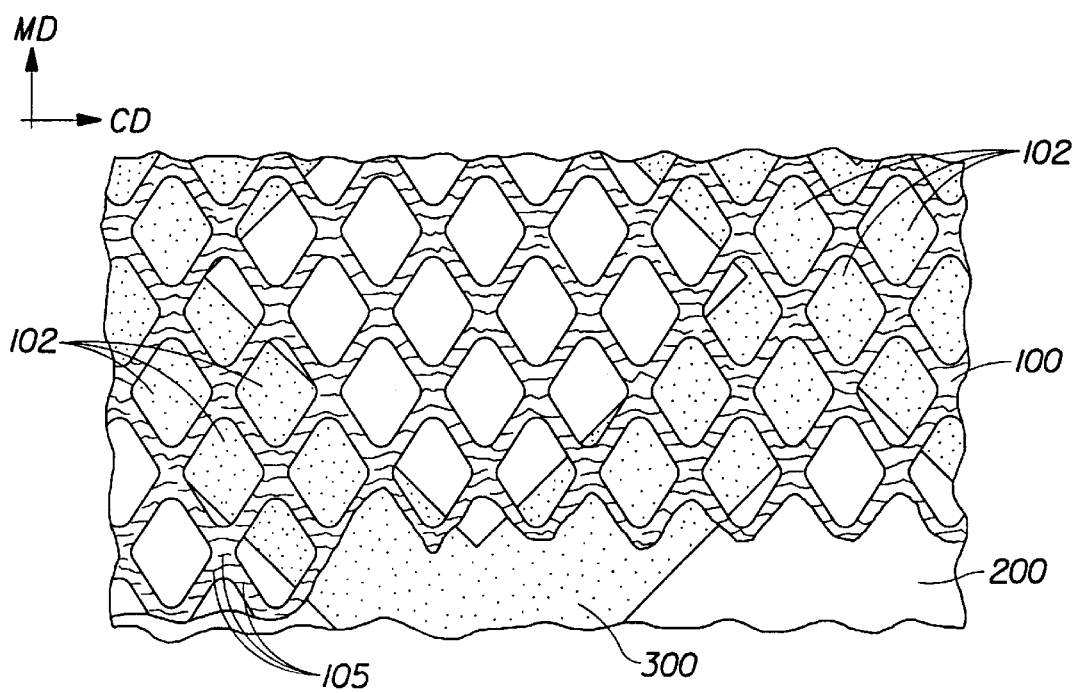
FIG. 4 is an illustration of a portion of the cleansing and conditioning article shown in FIG. 1, FIG. 4 being enlarged relative to FIG. 1 to illustrate the preferred apertures in the extensible first layer and creping ridges in the apertured layer.

In one preferred embodiment, the first layer 100 comprises a wetlaid paper web of cellulosic wood pulp fibers which is foreshortened at least about 4 percent, more preferably at least about 10 percent, and still more preferably at least about 20 percent, by dry creping. Referring to FIG. 4, the first layer 100 is shown comprising crepe ridges 105 corresponding to the foreshortening of the first layer 100. The machine direction (MD) and cross machine direction (CD) are indicated in FIGS. 1–4. The machine direction corresponds to the direction of manufacture of the paper web of first layer 100. The crepe ridges 105 are generally perpendicular to the machine direction, and generally parallel to the cross machine direction of the paper web of first layer 100.

The paper web of the first layer 100 can have a basis weight of between about 15 to about 65 grams per square meter. In a preferred embodiment, the basis weight of the first layer is between about 25 to about 45 grams per square meter, and in a more preferred embodiment, the basis weight of the first layer 100 is about 35 grams per square meter.

While not wishing to be bound by theory, it is believed that the paper strength can significantly alter the overall appearance of the complete article. The amount of crepe input to the first layer is directly proportional to the amount of planar expansion and thereby the amount of caliper generated upon wetting. However, if the wet strength of the paper article is insufficient, the "buckles" may collapse to form a more "wrinkled" product having less caliper. Therefore both crepe and wet strength can be adjusted to provide an amount of texture based on the intended use of the article. Wet burst measurements were measured by a Thwing-Albert Burst Tester model number 1300-77, which tested peak load of a fully wetted substrate. The test utilized a 0.5 in ball diameter, a 5 in/min ball velocity, and clamps the test sample around a 3.5 in. diameter circle perpendicular to the motion of the ball. Peak load wet burst strengths are between 100 and 1200 grams per ply. More preferably between 400 and 700 grams per ply and most preferably between 500 and 600 grams per ply.

In a more preferred embodiment, the first layer 100 comprises an apertured wetlaid paper web of cellulosic wood pulp fibers. The apertures 102 can be formed in the first layer 100 in any suitable manner. For instance, the apertures 102 can be formed in the first layer 100 during formation of the paper web of the first layer 100, or alternatively, after the paper web of the first layer 100 is manufactured. In one embodiment, the paper web of the first layer 100 is produced according to the teachings of one or more of the following U.S. patents, which patents are incorporated herein by reference: U.S. Pat. No. 5,245,025 issued Sep. 14, 1993 to Trokhan et al.; U.S. Pat. No. 5,277,761 issued Jan. 11, 1994 to Phan et al.; and U.S. Pat.

No. 5,654,076 issued Aug. 5, 1997 to Trokhan et al. In particular, U.S. Pat. No. 5,277,761 at Column 10 discloses formation of a paper web having a apertures.

Prior to wetting of the first layer, the creped first layer 100 can have between about 4 and about 300 apertures 102 per square inch, and more preferably between about 4 and about 100 apertures 102 per square inch. Wetting a creped paper web causes the web, if unrestrained, to expand in at least one direction, such as the machine direction, so that the number of apertures 102 per square inch after wetting can be smaller than the number of apertures per square inch prior to wetting. Similarly, when apertures are formed in a paper web, and the paper web is subsequently creped, the number of apertures per square inch prior to creping will be smaller than the number of apertures per square inch after creping. Accordingly references to paper web dimensions refer to dimensions after creping and prior to wetting.

The apertures 102 can comprise between about 15 and about 75 percent of the total surface of the first layer 100. The apertures 102 shown in FIG. 2 are bilaterally staggered (staggered in both the machine and cross machine directions) in a repeating, nonrandom pattern. In one embodiment, the first layer 100 comprises a paper web which is dry creped 25 percent (25 percent foreshortening) with greater than about 25 percent wet extensibility, and has about 40 to about 50 apertures, 102, per square inch, the apertures 102 having a length 103 (FIG. 4) of about 0.10 to about 0.18 inch and a width 104 of about 0.07 to about 0.15 inch, and a distance between apertures 106 of about 0.05 to about 0.08 inch.

The paper web is manufactured by first forming an aqueous papermaking furnish. The furnish comprises papermaking fibers, and can further comprise various additives. U.S. Pat. No. 5,223,096 issued Jun. 29, 1993 to Phan et al. is incorporated herein by reference for the purpose of disclosing various wood pulps and papermaking additives.

A suitable paper web for making the first layer 100 can be manufactured according to the following description. A papermaking furnish is prepared from water and highly refined Kraft pulp derived from northern softwoods (NSK), the paper furnish having a fiber consistency of about 0.2 percent (dry fiber weight divided by the total weight of the furnish equals 0.002). A dry strength additive such as carboxymethyl cellulose (CMC) is added to the 100% NSK furnish in the amount of about 5 pounds of CMC solids per ton of dry papermaking fibers. A wet strength additive such as Kymene 557H (available from Hercules, Inc. of Wilmington, Del.) is added to the furnish in the amount of about 28 pounds of Kymene solids per ton of dry papermaking fibers.

Figure 6:
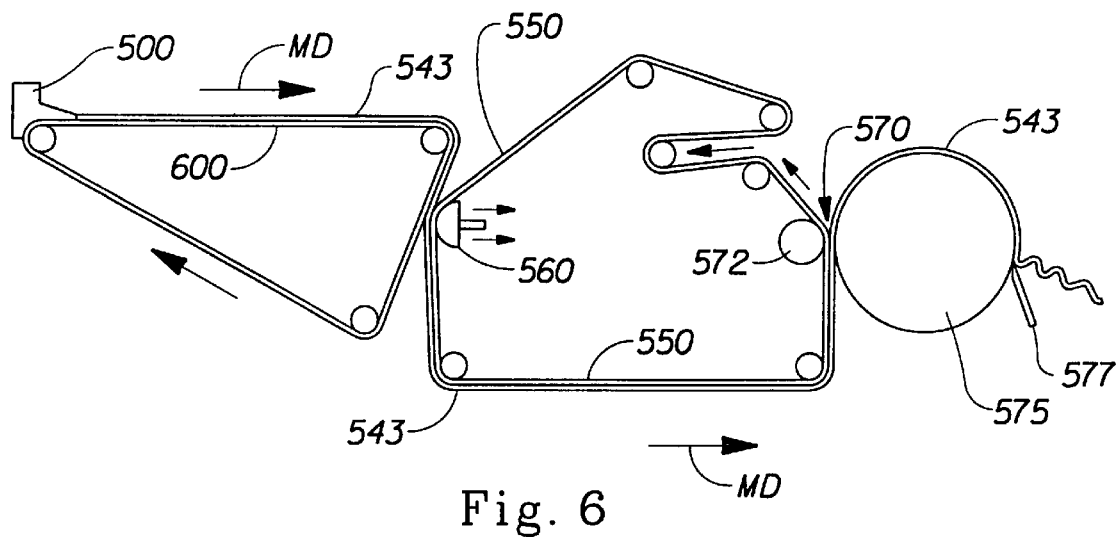
FIG. 6 is an illustration of a paper machine which can be used to make cellulosic paper webs that can be used in forming the substrate portion of the cleansing and conditioning articles herein.

Referring to FIG. 6, the furnish is deposited from a headbox 500 of a papermaking machine to a forming element 600 at a fiber consistency of about 0.2 percent. The forming element 600 is in the form of a continuous belt in FIG. 6. The slurry of papermaking fibers is deposited on the forming element 600, and water is drained from the slurry through the forming element 600 to form an embryonic web of papermaking fibers designated by reference numeral 543 in FIG. 6.

Figure 7:
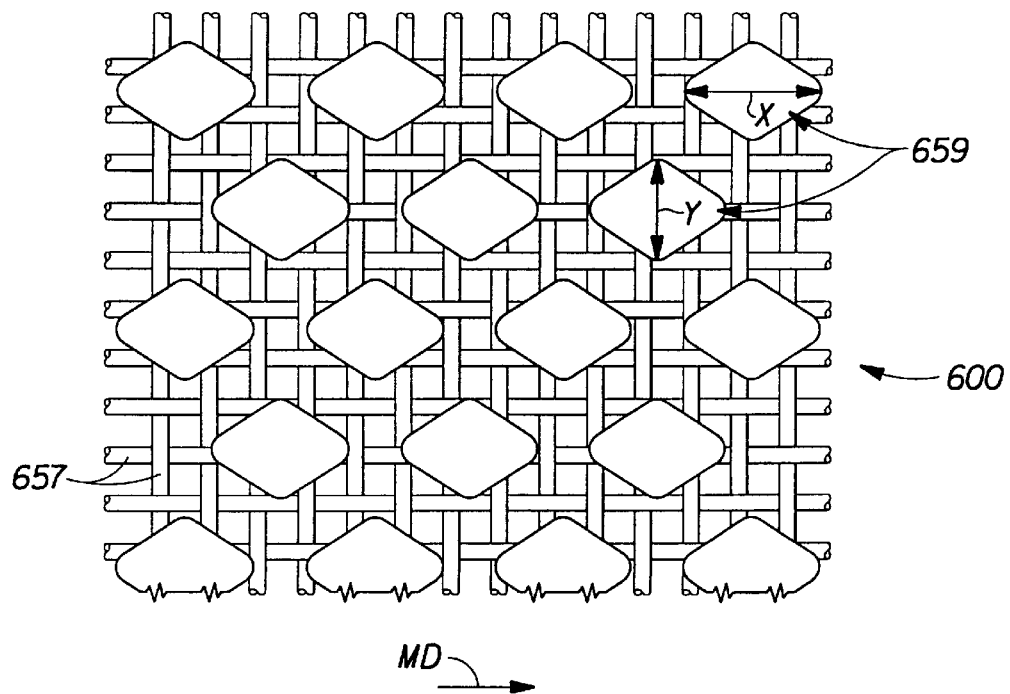
FIG. 7 is an illustration of a forming element which can be used to form a cellulosic paper web with apertures.

FIG. 7 shows a portion of the forming element 600. The forming element 600 has two mutually opposed faces. The face which is shown in FIG. 7 is the face which contacts the papermaking fibers of the web being formed. A description of a forming element of the type shown in FIG. 7 is provided in the above referenced U.S. Pat. Nos. 5,245,025; 5,277,761; and 5,654,076.

The forming element 600 has flow restriction members in the form of resin protuberances 659. The forming element 600 shown comprises a patterned array of protuberances 659 joined to a reinforcing structure 657, which may comprise a foraminous element, such as a woven screen or other apertured framework. The protuberances 659 extend above the reinforcing structure 657.

A suitable forming element 600 has about 37 protuberances 659 per square inch of surface of the forming element 600, with the protuberances 659 covering about 35 percent of the surface of the forming element 600, as viewed in FIG. 7, and the protuberances extending 0.0255 inches above the surface of the reinforcing structure 657. The protuberances can have a machine direction length X of about 0.1511 inch and a cross machine direction width Y of about 0.0924 inch.

The reinforcing structure 657 is substantially fluid pervious, while the protuberances 659 are substantially fluid impervious. Accordingly, as the liquid in the papermaking furnish drains through the forming element, the papermaking fibers in the furnish will be retained on the reinforcing structure 657, leaving apertures in the embryonic web 543 corresponding generally in size, shape and location to the size, shape and location of the protuberances 659.

Referring back to FIG. 6, the embryonic web 543 is transferred to a conventional dewatering felt 550 with the aid of a vacuum pick up shoe 560. The web 543 is transferred to the felt 550 at a fiber consistency of about 4 percent. The web 543 is carried on the felt 550 to a nip 570 formed between a vacuum pressure roll 572 and a Yankee dryer drum 575. The web 543 is dried on the Yankee drum 575 to a fiber consistency of about 96 percent, at which point the web is creped from the Yankee drum 575 with a doctor blade 577 having a bevel angle of about 25 degrees and an impact angle of about 81 degrees. The web is wound on a reel at a rate (lineal feet per second) which is 25 percent slower than the surface speed of the Yankee drum (reel speed equals 0.75 times the Yankee speed) to foreshorten the web about 25 percent. The foreshortened web can have a basis weight of about 33 grams per square meter, and a thickness of about 12 to 13 mils (0.012 to 0.013 inch) as measured with a confining pressure of 95 grams per square inch and a load foot having a diameter of 2 inches. The resulting foreshortened web can be used to form a first layer 100 having a wet extensibility of at least about 25 percent.

Second Layer:

The first layer 100 is joined to the second layer 200 to constrain extension of selected portions of the first layer 100 when the first layer is wetted. The second layer 200 has a lower wet extensibility than that of the first layer 100.

Suitable materials from which the second layer 200 can be formed include woven materials, nonwoven materials (including air-laid, wet-laid, carded and hydroentangled nonwoven materials), foams, battings, and the like. Particularly preferred materials are nonwoven webs having fibers or filaments distributed randomly as in "air-laying" or certain "wet-laying" processes, or with a degree of orientation, as in certain "wet-laying" and "carding" processes.

Nonwoven substrates made from synthetic materials useful in the present invention can be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 43 grams per square yard (gsy), available from Veratec, Inc., Walpole, Mass.; HEF 140-102, an apertured hydroentangled material containing about 50% rayon and 50% polyester, and having a basis weight of about 56 gsy, available from Veratec, Inc., Walpole, Mass.; Novonet® 149-616, a thermo-bonded grid patterned material containing about 100% polypropylene, and having a basis weight of about 50 gsy, available from Veratec, Inc., Walpole, Mass.; Novonet® 149-801, a thermo-bonded grid patterned material containing about 69% rayon, about 25% polypropylene, and about 6% cotton, and having a basis weight of about 75 gsy, available from Veratec, Inc. Walpole, Mass.; Novonet® 149-191, a thermo-bonded grid patterned material containing about 69% rayon, about 25% polypropylene, and about 6% cotton, and having a basis weight of about 100 gsy, available from Veratec, Inc. Walpole, Mass.; HEF Nubtex® 149-801, a nubbed, apertured hydroentangled material, containing about 100% polyester, and having a basis weight of about 70 gsy, available from Veratec, Inc. Walpole, Mass.; Keybak851V, a dry formed apertured material, containing about 75% rayon, about 25% acrylic fibers, and having a basis weight of about 43 gsy, available from Chicopee, New Brunswick, N.J.; Keybak® 1368, an apertured material, containing about 75% rayon, about 25% polyester, and having a basis weight of about 39 gsy, available from Chicopee, New Brunswick, N.J.; Duralace® 1236, an apertured, hydroentangled material, containing about 100% rayon, and having a basis weight from about 40 gsy to about 115 gsy, available from Chicopee, New Brunswick, N.J.; Duralace®1 5904, an apertured, hydroentangled material, containing about 1100% polyester, and having a basis weight from about 40 gsy to about 115 gsy, available from Chicopee, New Brunswick, N.J.; Chicopee® 5763, a carded hydroapertured material (8×6 apertures per inch), containing about 70% rayon, about 30% polyester, and a optionally a latex binder (EVA) of up to about 5% w/w, and having a basis weight from about 50 gsy to about 75 gsy, available form Chicopee, New Brunswick, N.J.; Chicopee® 9900 series (e.g., Chicopee 9931, 52 gsy, 50/50 rayon/polyester, and Chicopee 9950-42 gsy, 50/50 rayon/polyester), a carded, hydroentangled material, containing a fiber composition of from 50% rayon/50% polyester to 0% rayon/100% polyester or 100% rayon/0% polyester, and having a basis weight of from about 30 gsy to about 70 gsy, available form Chicopee, New Brunswick, N.J.; Sontara 8868, a hydroentangled material, containing about 50% cellulose and about 50% polyester, and having a basis weight of about 60 gsy, available from Dupont Chemical Corp. Preferred nonwoven substrate materials have a basis weight of about from 20 gsy to about 80 gsy, more preferably from about 30 gsy to about 70 gsy, and most preferably from about 35 gsy to about 65 gsy.

The substrate can be made into a wide variety of shapes and forms including flat pads, thick pads, thin sheets, ball-shaped implements, irregularly shaped implements, and having sizes ranging from a surface area of about a square inch to about hundreds of square inches. The exact size will depend upon the desired use and product characteristics. Especially convenient are square, circular, rectangular, or oval pads having a surface area of from about 1 $in^2$ to about 144 $in^2$, preferably from about 10 $in^2$ to about 120 $in^2$, and more preferably from about 30 $in^2$ to about 80 $in^2$. Furthermore, it is desirable for the substrates of the present invention to have rounded corners. This feature prevents the tendency of water to accumulate at the corners of an unrounded square substrate.

Bonding:

Selected portions of the first layer 100 are joined directly (or indirectly such as through a third component) to the second layer 200 in a predetermined bonding pattern to provide a plurality of bonded and unbonded regions of the first layer 100. In FIGS. 1–3, the bonded regions are designated 110, and the unbonded regions are designated 114. Each of the first and second layers 100 and 200 can have a machine direction, and the first and second layers can be bonded so that the machine direction of the first layer is generally parallel to the machine direction of the second layer.

The first layer 100 and the second layer 200 can be joined using any suitable method, including but not limited to adhesive bonding, mechanical bonding, thermal bonding, mechanical-thermal bonding, ultrasonic bonding, and combinations thereof. In particular, in a preferred embodiment, adhesive is applied by printing methods, such as a gravure printing, reverse gravure printing, screen printing, flexographic printing, and the like. In one preferred embodiment, EVA hot melt adhesive may be screen printed in a lattice pattern generally as shown in FIG. 1. The suitable screen for this embodiment is a 40 mesh Galvano screen manufactured by Rothtec Engraving Corp., New Bedford, Mass.

The adhesive is preferably water insoluble so that the article 20 can be wetted with water without delamination of the first and second layers. The adhesive is preferably also surfactant tolerant. By "surfactant tolerant" it is meant that the bonding characteristics of the adhesive are not degraded by the presence of surfactants. Suitable adhesives include EVA (ethylene vinyl acetate) based hot melt adhesives. One suitable adhesive is a hot melt adhesive commercially available as H1382-01 from Ato-Findley Adhesives of Wauwatosa, Wis.

With reference to FIGS. 1 and 2, the hot melt adhesive can be applied to the nonwoven second layer 200 in a continuous network defining a discontinuous plurality of unbonded regions 114. In one preferred embodiment, as shown in FIG. 1, the adhesive is applied as parallel, spaced apart lines in a first direction, intersected by parallel, spaced apart lines in a second direction. The intersecting lines form diamond-shaped patterns of unbonded regions in the final wipe. In the embodiment shown in FIG. 1, the hot melt adhesive can be applied in lines having a width of about 0.01 inch to about 0.5 inch, preferably about 0.05 to about 0.07 inch. The spacing between adjacent lines of adhesive can be about 0.2 inch to about 2.0, preferably about 0.4 to about 0.6 inches.

With reference to FIG. 3, the hot melt adhesive can be applied to the nonwoven second layer 200 in bands which extend generally parallel to the machine direction of the nonwoven second layer 200. The hot melt adhesive can be applied in stripes 310 having a width W (FIG. 3) of about 0.125 inch to about 1 inch. The spacing D between adjacent adhesive stripes can be about 0.125 inch to about 2 inches. In FIG. 3, four stripes 310A, 310B, 310C, and 310D are shown.

When applied as parallel stripes, lines, or bands, the adhesive can be applied to the nonwoven second layer 200 using a slot coating applicator. A suitable slot coating applicator is a Nordson MX series hot melter with extrusion head commercially available from the Nordson Company of Norcross, Ga. The 111382-01 adhesive referenced above can be applied to the second layer 200 at a temperature of about 350 Fahrenheit, at an application level of about 0.03 grams of adhesive per square inch. Immediately following application of the adhesive to the nonwoven second layer 200, the nonwoven second layer 200 and the paper first layer 100 can be bonded together by pressing the two layers 100 and 200 together with the adhesive disposed between the second layer 200 and the first layer 100. One suitable means for pressing the two layers 100 and 200 together is by passing the two layers through a nip formed between two rollers, with the rollers loaded to provide adequate nip pressure for bonding.

The resulting laminate of the first and second layers can have an average dry caliper of about 28.5 mils (0.0285 inch), an average wet caliper of about 32.1 mils (0.0321 inch), and a wet caliper to dry caliper ratio of about 1.1. The dry caliper, wet caliper, and wet caliper to dry caliper ratio are measured as described below under "Wet Caliper to Dry Caliper Ratio."

Wet Extensiblity Test

The wet extensibility of a layer, such as the layer 100 or the layer 200, is determined using the following procedure. Samples are conditioned at 70 degrees Fahrenheit and 50 percent relative humidity for two hours prior to testing.

First, the direction of greatest wet extensibility in the plane of the layer is determined. For dry creped paper webs, this direction will be parallel to the machine direction, and generally perpendicular to the crepe ridges.

If the direction of greatest wet extensibility is not known, the direction can be determined by cutting seven samples from a sheet with sample lengths oriented between 0 degrees and 90 degrees, inclusive, with respect to a reference line drawn on the sheet. The samples are then measured as set forth below to determine the direction of greatest wet extensibility.

Once the direction of the greatest wet extensibility is determined, 8 samples are cut to have a length of about 7 inches measured parallel to the direction of greatest wet extensibility, and a width of at least 1 inch. The samples are cut from unbonded portions of the layers 100 and 200, or, if unbonded portions having the above dimensions cannot be cut from the article 20, then samples are cut from the layers 100 and 200 prior to bonding the layers together. Two marks are placed on each sample, such as with an ink pen. The marks are spaced apart 5 inches as measured parallel to the direction of greatest wet extensibility. This 5 inch length is the initial dry test length of the sample.

Each sample is thoroughly wetted by submerging the sample in distilled water for 30 seconds in a water bath. Each sample is removed from the water bath and immediately supported to hang vertical y so that a line through the two marks is generally vertical. The wet sample is supported such that the support does not interfere with ex tension between the two marks (e.g. with a clip which does not contact the sample between the two marks). The wet test length of the sample is the distance between the two marks. The distance is measured within 30 seconds of re moving the sample from the water bath.

For each sample, the percent wet extension is calculated as

Sample Wet Extension=(wet test length−initial dry test length)/(initial dry test length)×100

For example, for a measured wet test length of 6.5 inches and an initial dry test length of 5.0 inches, the wet extension is ((6.5−5)/5 )×100=30 percent.

The wet extensibility of the samples is the average of 8 calculated values of sample wet extension.

Wet Caliper to Dry Caliper Ratio

The wet caliper to dry caliper ratio is measured using a Thwing-Albert Instrument Co. Electronic Thickness Tester Model II, using the following procedure. Samples are conditioned at 70 degrees Fahrenheit and 50 percent relative humidity for two hours prior to testing.

The dry caliper of the article 20 is measured using a confining pressure of 95 grams per square inch and a load foot having a diameter of 2 inches. The dry caliper is measured for eight samples. For each sample, the caliper is measured with the load foot centered on an unbonded region of the first layer 100. The eight caliper measurements are averaged to provide an average dry caliper.

Each sample is the n wetted by submerging the sample in a distilled water bath for 30 seconds. The sample is then removed from the water bath and drained by hanging 30 vertically for about five seconds. The caliper of the wet sample is measured within 30 seconds of removing the sample from the bath. The wet caliper is measured in the same location in which the dry caliper was previously measured. The eight wet caliper measurements are averaged to provide an average wet caliper. The wet caliper to dry caliper ratio is the average wet caliper divided by the average dry caliper.

The wet caliper to dry caliper ratio is the average wet caliper divided by the average dry caliper.

Lathering Surfactant

The articles of the present invention comprise one or more lathering surfactants which are added onto or impregnated into the substrate. Preferred articles of the present invention comprise a sufficient amount of one or more lathering surfactants such that the articles are capable of generating $\geq 30$ ml of Lather Volume (medium hardness water at 95° C.) according to the Lather Volume Test described below. Preferably, the articles of the present invention comprise from about 0.5% to about 12.5%, more preferably from about 0.75% to about 11%, and most preferably from about 1% to about 10%, based on the weight of the water insoluble substrate, of a lathering surfactant.

By a lathering surfactant is meant a surfactant, which when combined with water and mechanically agitated generates a foam or lather sufficient to cause the article, as a whole, to lather. Preferably, these surfactants or combinations of surfactants should be mild, which means that these surfactants provide sufficient cleansing or detersive benefits but do not overly dry the skin or hair, and yet meet the lathering criteria described above.

A wide variety of lathering surfactants are useful herein and include those selected from the group consisting of anionic lathering surfactants, nonionic lather surfactants, amphotheric lathering surfactants, and mixtures thereof. Generally, the lathering surfactants do not strongly interfere with deposition of the conditioning agents, e.g., are fairly water soluble, and usually have an HLB value of above 10. Cationic surfactants can also be used as optional components, provided they do not negatively impact the overall lathering characteristics of the required, lathering surfactants.

Anionic Lathering Surfactants

Nonlimiting examples of anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929, 678, to Laughlin et al., issued Dec. 30, 1975, all of which are incorporated by reference herein in their entirety.

A wide variety of anionic lathering surfactants are useful herein. Nonlimiting examples of anionic lathering surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred. The alkoyl isethionates typically have the formula RCO—OCH2CH2SO3M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulae ROSO3M and RO(C2H4O)xSO3M, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

R1—SO3—M wherein R1 is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Other anionic materials include alkanoyl sarcosinates corresponding to the formula RCON(CH3)CH2CH2CO2M wherein R is alkyl or alkenyl of about 10 to about 20 carbon atoms, and M is a water-soluble cation such as ammonium, sodium, potassium and alkanolamine (e.g., triethanolamine), a preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates which are based on taurine, which is also known as 2-aminoethanesulfonic acid. Especially useful are taurates having carbon chains between C8 and C16. Examples of taurates include N-alkyltaurines such as the one prepared by reacting dodecylamine with sodium isethionate according to the teaching of U.S. Pat. No. 2,658,072 which is incorporated herein by reference in its entirety. Further nonlimiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between C8 and C16. Nonlimiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are glutamates, especially those having carbon chains between C8 and C16. Nonlimiting examples of glutamates include ammonium, sodium, potassium and alkanolamine (e.g., triethanolamine) salts of lauroyl glutamate, myristoyl glutamate, and cocoyl glutamate.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein is ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Nonionic Lathering Surfactants

Nonlimiting examples of nonionic lathering surfactants for use in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety.

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Alkyl glucosides and alkyl polyglucosides are useful herein, and can be broadly defined as condensation articles of long chain alcohols, e.g. C8-30 alcohols, with sugars or starches or sugar or starch polymers, i.e., glycosides or polyglycosides. These compounds can be represented by the formula (S)n—O—R wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8-20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein: $R^1$ is H, C1–C4 alkyl, 2-hydroxyethyl, 2-hydroxypropyl, preferably C1–C4 alkyl, more preferably methyl or ethyl, most preferably methyl; $R^2$ is C5–C31 alkyl or alkenyl, preferably C7–C19 alkyl or alkenyl, more preferably C9–C17 alkyl or alkenyl, most preferably C11–C15 alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the R2CO— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A.M. Schwartz, issued Mar. 8, 1955; and U.S. Pat. No. 1,985,424, to Piggott, issued Dec. 25, 1934; which are incorporated herein by reference in their entirety.

Other examples of nonionic surfactants include amine oxides. Amine oxides correspond to the general formula R1R2R3NO, wherein R1 contains an alkyl, alkenyl or monohydroxy alkyl radical of from about 8 to about 18 carbon atoms, from 0 to about 10 ethylene oxide moieties, and from 0 to about 1 glyceryl moiety, and R2 and R3 contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethyl-bexadecylamine oxide.

Nonlimiting examples of preferred nonionic surfactants for use herein are those selected form the group consisting of C8–C14 glucose amides, C8–C14 alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the RCONH(CH2)3 radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

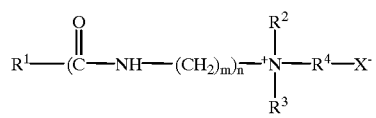

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine)

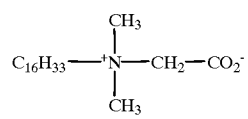

Cocamidopropylbetaine

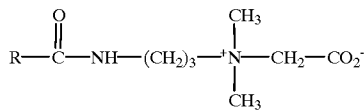

wherein R has from about 9 to about 13 carbon atoms

Cocamidopropyl hydroxy sultaine

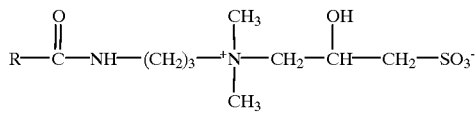

wherein R has from about 9 to about 13 carbon atoms,

Examples of other useful amphoteric surfactants are alkyliminoacetates, and iminodialkanoates and aminoalkanoates of the formulas RN[CH2)mCO2M]2 and RNH(CH2)mCO2M wherein m is from 1 to 4, R is a C8–C22 alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof; wherein the nonionic lathering surfactant is selected from the group consisting of lauramine oxide, cocoamine oxide, decyl polyglucose, lauryl polyglucose, sucrose cocoate, C12-14 glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

Lather Volume Test

The articles of the present invention preferably comprise enough of the lathering surfactant such that the articles are capable of generating greater than or equal to about 30 ml, more preferably greater than or equal to about 50 ml, even more preferably greater than or equal to about 75 ml, and most preferably greater than or equal to about 150 ml of Average Lather Volume. The Average Lather Volume is a measurement determined by the Lather Volume Test. This test provides a consistent measurement of the volume of lather/foam generated by the articles described herein. The Lather Volume Test protocol is described as follows:

(1) Hands are washed with Ivory bar before conducting the test. This step removes any soils which may affect the accuracy of the measurement.

(2) The test article is held open in the non-dominant hand with the edges turned up.

(3) 10 m. of water (medium hardness of about 8–10 grains per gallon) at 95° C. is added onto the test article via a 10 cc syringe or a Brinkmann repipetter.

(4) The lather is then generated by rubbing the test article with the dominant hand in a circular motion between the palms for 6 seconds (~2 rotations per second), using moderate pressure (e.g., 4 oz.), and allowing the article to ball-up between the palms of the hand.

(5) The test article is then held open in the non-dominant hand and an additional 10 ml of water (medium hardness of about 8–10 grains per gallon) at 95° C. is added onto the test article via a 10 cc syringe or a Brinkmann repipetter. The wetted article is again rubbed with the dominant had (3 rotations) using moderate force (e.g., 4 oz.) so that the test article becomes balled-up between the palms.

(6) The test article is then opened and rubbed 5 times by holding one edge of the article in one hand and rotating the hand holding the other side to further activate lather.

(7) The test article is then flipped over and Step #6 is repeated using the other hand.

(8) The lather is gathered by holding the test article in a cupped hand and scraping the lather off the test article with the other hand, being careful to only scrape lather from the test article. The lather from the test article is placed into a graduated cylinder or beaker big enough to hold the generated lather. This procedure is repeated 5 times on the same test article, and the lather from each iteration is accumulated in the same graduated cylinder or beaker. The total accumulated lather from these iterations is designated as the Lather Volume.

(9) To achieve consistent results, the Average Lather Volume is reported as the average of three test sample replications of Steps 1–8.

Conditioning Component

The articles of the present invention can further comprise a conditioning component which is useful for providing a conditioning benefit to the skin or hair during the use of the article. The conditioning component comprises from about 0.05% to about 99%, preferably from about 0.1% to about 50%, and more preferably from about 1% to about 25% by weight of said water insoluble substrate.

The conditioning component of the present invention can comprise: a water soluble conditioning agent; an oil soluble conditioning agent; a conditioning emulsion; or any combination or permutation of the three. The oil soluble conditioning agent is selected from one or more oil soluble conditioning agents such that the weighted arithmetic mean solubility parameter of the oil soluble conditioning agent is less than or equal to 10.5. The water soluble conditioning agent is selected from one or more water soluble conditioning agents such that the weighted arithmetic mean solubility parameter of the water soluble conditioning agent is greater than 10.5. It is recognized, based on this mathematical definition of solubility parameters, that it is possible, for example, to achieve the required weighted arithmetic mean solubility parameter, i.e. less than or equal to 10.5, for an oil soluble conditioning agent comprising two or more compounds if one of the compounds has an individual solubility parameter greater than 10.5. Conversely, it is possible to achieve the appropriate weighted arithmetic mean solubility parameter, i.e. greater than 10.5, for a water soluble conditioning agent comprising two or more compounds if one of the compounds has an individual solubility parameter less than or equal to 10.5.

Solubility parameters are well known to the formulation chemist of ordinary skill in the art and are routinely used as a guide for determining compatibilities and solubilities of materials in the formulation process.

The solubility parameter of a chemical compound, 6, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[ \frac{\sum_i E_i}{\sum_i m_i} \right]^{1/2}$$

wherein $\sum_i E_i$=the sum of the heat of vaporization additive group contributions, and $\sum_i m_i$=the sum of the molar volume additive group contributions Standard tabulations of heat of vaporization and molar volume additive group contributions for a wide variety of atoms and groups of atoms are collected in Barton, A.F.M. Handbook of Solubility Parameters, CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", Polymer Engineering and Science, vol. 14, no. 2, pp. 147–154 (February 1974), which is incorporated by reference herein in its entirety.

Solubility parameters obey the law of mixtures such that the solubility parameter for a mixture of materials is given by the weighted arithmetic mean (i.e. the weighted average) of the solubility parameters for each component of that mixture. See, Handbook of Chemistry and Physics, 57th edition, CRC Press, p. C-726 (1976–1977), which is incorporated by reference herein in its entirety.

Formulation chemists typically report and use solubility parameters in units of $(cal/cm^3)^{1/2}$. The tabulated values of additive group contributions for heat of vaporization in the Handbook of Solubility Parameters are reported in units of kJ/mol. However, these tabulated heat of vaporization values are readily converted to cal/mol using the following well-known relationships:

1 J/mol=0.239006 cal/mol and 1000 J=1 kJ.

See Gordon, A. J. et al., The Chemist's Companion, John Wiley & Sons, pp. 456–463, (1972), which is incorporated by reference herein in its entirety.

Solubility parameters have also been tabulated for a wide variety of chemical materials. Tabulations of solubility parameters are found in the above-cited Handbook of Solubility Parameters. Also, see "Solubility Effects In Product, Package, Penetration, And Preservation", C. D. Vaughan, Cosmetics and Toiletries, vol. 103, October 1988, pp. 47–69, which is incorporated by reference herein in its entirety.

Nonlimiting examples of conditioning agents useful as oil soluble conditioning agents include those selected from the group consisting of mineral oil, petrolatum, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol C4–C20 alkyl ethers, di C8–C30 alkyl ethers, and mixtures thereof.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth 10 Edition, Entry 7047, p. 1033 (1983); Schindler, Drug. Cosmet. Ind., 89, 36–37, 76, 78–80, 82 (1961); and International Cosmetic Ingredient Dictionary, Fifth Edition, vol. 1, p. 537 (1993), which are incorporated by reference herein in their entirety.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a C22 hydrocarbon), hexadecane, isohexadecane (a commercially available hydrocarbon sold as Permethyl® 101A by Presperse, South Plainfield, N.J.). Also useful are the C7–C40 isoparaffins, which are C7–C40 branched hydrocarbons.

Also useful are C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

Also useful are various C1–C30 monoesters and polyesters of glycerin and related materials. These esters are derived from glycerin and one or more carboxylic acid moities. Depending on the constituent acid and glycerin, these esters can be in either liquid or solid form at room temperature. Nonlimiting examples of solid esters include: glyceryl tribehenate, glyceryl stearate, glyceryl palmitate, glyceryl distearate, glyceryl dipalmitate.

Also useful are various C1–C30 monoesters and polyesters of sugars and related materials. These esters are derived from a sugar or polyol moiety and one or more carboxylic acid moities. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates-:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991, which is incorporated by reference herein in its entirety. The polyalkylsiloxanes correspond to the general chemical formula $R3SiO[R2SiO]xSiR3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH2)3SiO½]x[SiO2]y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R3SiO[R2SiO]xSiR2011$ and $HOR2SiO[R2SiO]xSiR2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, dioctyl ether, dodecyl octyl ether, and mixtures thereof.

Nonlimiting examples of conditioning agents useful as water soluble conditioning agents include those selected from the group consisting of polyhydric alcohols, polypropylene glycols, polyethylene glycols, ureas, pyrolidone carboxylic acids, ethoxylated and/or propoxylated C3–C6 diols and triols, alpha-hydroxy C2–C6 carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful water soluble conditioning agents include materials such as urea; guanidine; glycolic acid and glycolate salts (e.g. ammonium and quaternary alkyl ammonium); lactic acid and lactate salts (e.g. ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; and mixtures thereof. Also useful are materials such as aloe vera in any of its variety of forms (e.g., aloe vera gel), chitin, starch-grafted sodium polyacrylates such as Sanwet (RTM) IM-1000, IM-1500, and IM-2500 (available from Celanese Superabsorbent Materials, Portsmouth, Va.); lactamide monoethanolamine; acetamide monoethanolamine; and mixtures thereof. Also useful are propoxylated glycerols as described in propoxylated glycerols described in U.S. Pat. No. 4,976,953, to Orr et al., issued Dec. 11, 1990, which is incorporated by reference herein in its entirety.

The conditioning component of the present invention may also comprise a conditioning emulsion which is useful for providing a conditioning benefit to the skin or hair during the use of the article. The term "conditioning emulsion" as used herein means the combination of an internal phase comprising a water soluble conditioning agent that is enveloped by an external phase comprising an oil soluble agent. In preferred embodiments, the conditioning emulsion would further comprise an emulsifier. The conditioning emulsion comprises from about 0.25% to about 150%, preferably from about 0.5% to about 100%, and more preferably from about 1% to about 50% by weight of said water insoluble substrate. By a conditioning emulsion is meant a combination of an internal phase comprising a water soluble conditioning agent that is enveloped by an external phase comprising an oil soluble agent. In preferred embodiments, the conditioning emulsion would further comprise an emulsifier.

The conditioning emulsion comprises (i) an internal phase comprising water soluble conditioning agents as described above, and (ii) an external phase comprising oil soluble agents as described hereinbefore in the oil soluble conditioning agent section or hereinafter in the "Materials Used to Increase Lipid Hardness Value" section. In further embodiments, the conditioning emulsion further comprises an emulsifier capable of forming an emulsion of said internal and external phases. Although an emulsifier capable of forming an emulsion of the internal and external phases is preferred in the present invention, it is recognized in the art of skin care formulations that a water soluble conditioning agent can be enveloped by an oil soluble agent without an emulsifier. As long as the water soluble conditioning agent is enveloped by the oil soluble agent, thereby protected from being rinsed away during the cleansing process, the composition would be within the scope of the present invention.

The internal phase can optionally comprise other water-soluble or dispersible materials that do not adversely affect the stability of the conditioning emulsion. One such material is a water-soluble electrolyte. The dissolved electrolyte minimizes the tendency of materials present in the lipid phase to also dissolve in the water phase. Any electrolyte capable of imparting ionic strength to the internal phase can be used. Suitable electrolytes include the water soluble mono-, di- or trivalent inorganic salts such as water-soluble halides, e.g., chlorides, nitrates and sulfates of alkali metals and alkaline earth metals. Examples of such electrolytes include sodium chloride, calcium chloride, sodium sulfate, magnesium sulfate, and sodium bicarbonate. The electrolyte will typically be included in a concentration in the range of from about 1 to about 20% of the internal phase.

Other water-soluble or dispersible materials that can be present in the internal phase include thickeners and viscosity modifiers. Suitable thickeners and viscosity modifiers include water-soluble polyacrylic and hydrophobically modified polyacrylic resins such as Carbopol and Pemulen, starches such as corn starch, potato starch, tapioca, gums such as guar gum, gum arabic, cellulose ethers such as hydroxypropyl cellulose, hydroxyethyl cellulose, carboxymethyl cellulose, and the like. These thickeners and viscosity modifiers will typically be included in a concentration in the range of from about 0.05 to about 0.5% of the internal phase.

Other water soluble or dispersible materials that can be present in the internal water phase include polycationic polymers to provide steric stabilization at the water-lipid interface and nonionic polymers that also stabilize the water-in-lipid-emulsion. Suitable polycationic polymers include Reten 201, Kymene 557H® and Acco 7112. Suitable nonionic polymers include polyethylene glycols (PEG) such as Carbowax. These polycationic and nonionic polymers will typically be included in a concentration in the range of from about 0.1 to about 1.0% of the internal phase.

Preferred embodiments of the present invention which contain conditioning emulsions comprise an emulsifier capable of forming an emulsion of the internal and external phases. In the emulsions of the present invention, the emulsifier is included in an effective amount. What constitutes an "effective amount" will depend on a number of factors including the respective amounts of the oil soluble agents, the type of emulsifier used, the level of impurities present in the emulsifier, and like factors. Typically, the emulsifier comprises from about 0.1% to about 20%, preferably from about 1% to about 10%, and more preferably from about 3% to about 6% by weight of the conditioning emulsion.

The emulsifiers useful in the present invention typically are oil soluble or miscible with the oil soluble external phase materials, especially at the temperature at which the lipid material melts. It also should have a relatively low HLB value. Emulsifiers suitable for use in the present invention have HLB values typically in the range of from about 1 to about 7 and can include mixtures of different emulsifiers. Preferably, these emulsifiers will have HLB values from about 1.5 to about 6, and more preferably from about 2 to about 5.

A wide variety of emulsifiers are useful herein and include, but not limited to, those selected from the group consisting of sorbitan esters, glyceryl esters, polyglyceryl esters, methyl glucose esters, sucrose esters, ethoxylated fatty alcohols, hydrogenated castor oil ethoxylates, sorbitan ester ethoxylates, polymeric emulsifiers, and silicone emulsifiers.

Sorbitan esters are useful in the present invention. Preferable are sorbitan esters of C16–C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83), sorbitan monoisostearate (e.g., CRILL® 6 made by Croda), sorbitan stearates (e.g., SPAN® 60), sorbitan trioleate (e.g., SPAN(85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Other suitable emulsifiers for use in the present invention include, but is not limited to, glyceryl monoesters, preferably glyceryl monoesters of C16–C22 saturated, unsaturated and branched chain fatty acids such as glyceryl oleate, glyceryl monostearate, glyceryl monopalmitate, glyceryl monobehenate, and mixtures thereof; polyglyceryl esters of C16–C22 saturated, unsaturated and branched chain fatty acids, such as polyglyceryl-4 isostearate, polyglyceryl-3 oleate, diglycerol monooleate, tetraglycerol monooleate and mixtures thereof; methyl glucose esters, preferably methyl glucose esters of C16–C22 saturated, unsaturated and branched chain fatty acids such as methyl glucose dioleate, methyl glucose sesquiisostearate, and mixtures thereof; sucrose fatty acid esters, preferably sucrose esters of C12–C22 saturated, unsaturated and branched chain fatty acids such as sucrose stearate, sucrose trilaurate, sucrose distearate (e.g., Crodesta® F10), and mixtures thereof; C12–C22 ethoxylated fatty alcohols such as oleth-2, oleth-3, steareth-2, and mixtures thereof; hydrogenated castor oil ethoxylates such as PEG-7 hydrogenated castor oil; sorbitan ester ethoxylates such as PEG-40 sorbitan peroleate, Polysorbate-80, and mixtures thereof; polymeric emulsifiers such as ethoxylated dodecyl glycol copolymer; and silicone emulsifiers such as laurylmethicone copolyol, cetyldimethicone, dimethicone copolyol, and mixtures thereof.

In addition to these primary emulsifiers, the compositions of the present invention can optionally contain a coemulsifier to provide additional water-lipid emulsion stability. Suitable coemulsifiers include, but is not limited to, phosphatidyl cholines and phosphatidyl choline-containing compositions such as lecithins; long chain C16–C22 fatty acid salts such as sodium stearate; long chain C16–C22 dialiphatic, short chain C1–C4 dialiphatic quaternary ammonium salts such as ditallow dimethyl ammonium chloride and ditallow dimethyl ammonium methylsulfate; long chain C16–C22 dialkoyl(alkenoyl)-2-hydroxyethyl, short chain C1–C4 dialiphatic quaternary ammonium salts such as ditallowoyl-2-hydroxyethyl dimethyl ammonium chloride; the long chain C16–C22 dialiphatic imidazolinium quaternary ammonium salts such as methyl-1-tallow amido ethyl-2-tallow imidazolinium methyl sulfate and methyl-1-oleylamido ethyl-2-oleyl imidazolinium methylsulfate; short chain C1–C4 dialiphatic, long chain C16–C22 monoaliphatic benzyl quaternary ammonium salts such as dimethyl stearyl benzyl ammonium chloride, and synthetic phospholipids such as stearamidopropyl PG-dimonium chloride (Phospholipid PTS from Mona Industries).

Lipid Hardness Value

In embodiments further comprising a conditioning component, the article will preferably have a minimum lipid hardness value about 0.02 kg. The lipid hardness value is a physical hardness measurement of the combination of all conditioning agents within the conditioning component. It is believed that increasing the lipid hardness value increases deposition consistency of the conditioning agents despite variations in lathering techniques employed by the consumer. It is believed that increasing conditioning component hardness decreases transfer within the substrate and also decreases emulsification of the conditioning agents by the surfactants during the lathering step. As a result, more of the conditioning agents remain available for mechanical transfer via contact with the skin or hair.

The conditioning component of the present invention has a lipid hardness value of greater than about 0.02 kg, preferably greater than about 0.05, and more preferably greater than about 0.10. Preferably, the lipid hardness value of the conditioning component should not be greater than about 5.00 kg., more preferably about 4.00 kg, most preferably 3.00, because hardness levels beyond this point can negatively affect deposition of the conditioning agents in the conditioning component to the skin or hair.

Lipid Hardness Test

The lipid hardness value is measured by a test traditionally used to measure bar soap hardness. A Chatillon force gauge is employed to measure the hardness value of a 5–8 oz. sample of the conditioning component. Several readings are taken, each on a fresh sample, to obtain an average value. The Chatillon force gauge model no. DFISI00 is manufactured by Chatillon Corporation which is located in Greensboro, N.C.

Materials Used to Increase Lipid Hardness Value

The cleansing and conditioning articles of the present invention may comprise a hardening material used in combination with the conditioning agents comprising the conditioning component described hereinbefore. Many materials can be used as both a conditioning agent and as a lipid hardening material. In fact, any solid conditioning agent, described hereinbefore, may be used as a lipid hardening material. The amount of the hardening material needed to achieve the minimum lipid hardness value of 0.02 kg. is dependent upon the particular material used and can be easily determined by one of ordinary skill in the art. The hardening material can be used as an individual hardening material or a combination of hardening materials, and is included at concentrations ranging from about 0.1% to about 99.9%, preferably from about 0.5% to about 75%, more preferably from about 1% to about 50%, even more preferably from about 2% to about 25%, by weight of the conditioning component.

As used herein the term "hardening materials" refers to those materials which have a melting point above about 30° C., preferably above about 30° C. to about 250° C., more preferably from about 37° C. to about 100° C., even more preferably from about 37° C. to about 80° C.

Any material may be used to increase the lipid hardness value of the conditioning component provided that the following criteria are met: (i) the material must be soluble in the conditioning agents of the conditioning component and (ii) the material must have a melting point of greater than 20° C. (e.g., be a solid at room temperature). Examples of suitable hardening materials include, but are not limited to, petrolatum, highly branched hydrocarbons, fatty alcohols, fatty acid esters, vegetable oils, hydrogenated vegetable oils, polypropylene glycols, alpha-hydroxy fatty acids, fatty acids having from about 10 to about 40 carbon atoms, alkyl amides of di and/or tri-basic carboxylic acids, n-acyl amino acid derivatives, and mixtures thereof. Hardening materials useful in the present invention are further described in U.S. Pat. No. 4,919,934, to Deckner et al., issued Apr. 24 1990, which is incorporated herein by reference in its entirety.

Suitable highly branched hydrocarbons for use herein include hydrocarbon compounds having from about 17 to about 40 carbon atoms. Nonlimiting examples of these hydrocarbon compounds include squalane, cholesterol, lanolin, docosane (i.e., a C22 hydrocarbon), and isoparaffins.

Suitable fatty alcohols for use herein include monohydric alcohols, ethoxylated fatty alcohols, and fatty alcohol esters, excluding the ethoxylated fatty alcohols and fatty alcohol esters useful as emulsifiers herein. Specific examples of commercially available fatty alcohols include, but are not limited to, Unilin 550, Unilin 700, Unilin 425, Unilin 400, Unilin 350, and Unilin 325, all supplied by Petrolite. Suitable ethoxylated fatty alcohols include, but are not limited to, Unithox 325, Unithox 400, and Unithox 450, Unithox 480, Unithox 520, Unithox 550, Unithox 720, Unithox 750, all of which are available from Petrolite. Non-limiting examples of suitable esters of fatty alcohols include tri-isostearyl citrate, ethyleneglycol di-12-hydroxystearate, tristearylcitrate, stearyl octanoate, stearyl heptanoate, trilaurylcitrate.

Suitable fatty acid esters for use herein include ester waxes, monoglycerides, diglycerides, triglycerides and mixtures thereof. Non-limiting examples of suitable ester waxes include stearyl stearate, stearyl behenate, palmityl stearate, stearyl octyldodecanol, cetyl esters, cetearyl behenate, behenyl behenate, ethylene glycol distearate, ethylene glycol dipalmitate, and beeswax. Examples of commercial ester waxes include Kester waxes from Koster Keunen, Crodamol SS from Croda and Demalcare SPS from Rhone Poulenc.

Animal-based fats and oils and vegetable oils and hydrogenated vegetable oils which are solid or semi-solid at ambient temperatures of from about 20° C. to about 25° C. are also useful herein as hardening materials. Examples of suitable vegetable oils and hydrogenated vegetable oils include butterfat, chicken fat, goose fat, horse fat, lard (fatty tissue) oil, rabbit fat, sardine oil, tallow (beef), tallow (mutton), chinese vegetable tallow, babassu oil, cocoa butter, coconut oil, palm oil, palm kernal oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, derivatives thereof and mixtures thereof.

Suitable polypropylene glycols for use herein include C4–C16 alkyl ethers of polypropylene glycols, and C1–C16 carboxylic acid esters of polypropylene glycols. Nonlimiting examples of these materials include PPG-14 butyl ether, PPG-15 stearyl ether, PPG-9, PPG-12, PPG-15, PPG-17, PPG-20, PPG-26, PPG-30, PPG-34, and mixtures thereof.

Examples of suitable alpha-hydroxy fatty acids and fatty acids having from about 10 to about 40 carbon atoms include 12-hydroxystearic acid, 12-hydroxylauric acid, 16-hydroxyhexadecanoic acid, behenic acid, eurcic acid, stearic acid, caprylic acid, lauric acid, isostearic acid, and mixtures thereof. Examples of some suitable fatty acids are further described in U.S. Pat. No. 5,429,816, issued to Hofrichter et al. on Jul. 4, 1995; and U.S. Pat. No. 5,552,136, issued to Motley on Sep. 3, 1996, which descriptions are incorporated herein by reference.

Suitable alkyl amides of di and/or tri-basic carboxylic acids for use herein include disubstituted or branched monoamides, monosubstituted or branched diamides, triamides, and mixtures thereof. Some specific examples of alkyl amides of di- and tri-basic carboxylic acids include, but are not limited to, alkyl amides of citric acid, tricarballylic acid, aconitic acid, nitrilotriacetic acid and itaconic acid such as 1,2,3-propane tributylamide, 2-hydroxy-1,2,3-propane tributylamide, 1-propene-1,2,3-trioctylamide, N,N', N"-tri(methyldecylamide)amine, 2 docecyl-N,N'-dibutylsuccinamide, and mixtures thereof. Other suitable amides include the n-acyl amino acid derivatives described in U.S. Pat. No. 5,429,816, issued to Hofrichter et al. on Jul. 4, 1995.

Also suitable for use in the present invention are waxes having a HLB of from about 1 to about 10, preferably from about 6 and most preferably from about 5. The HLB (short for "Hydrophile-Lipophile Balance") value system is fully described, and values for various materials are provided, in the publication The Time-Saving Guide to Emulsifier Selection (published by ICI Americas Inc., Wilmington, Del.; 1984), the disclosure of which are incorporated herein by reference in their entirety.

Useful ester waxes include C10–C40 fatty acid, diesters, of C10–C40 fatty acids where the alcohol is propylene glycol, ethylene glycol, polyethylene glycol, polypropylene glycol, polyglycerin, or glycerin, triglycerides or diglycerides of C10–C40 fatty acids, pentaerythritol tri-ortetra-esters of C10–C40 fatty acids, C10–C40 fatty acids of sorbitan triesters, C10–C40 fatty acids of sucrose polyesters having 3–8 moles of substitution, myristyl myristate, paraffin, synthetic waxes such as Fischer-Tropsche waxes, microcrystalline waxes, castor wax, partially hydrogenated vegetable oils, behenyl behenrate and myristyl propionate and mixtures thereof.

Useful diester waxes include Synchrowax ERL-C (C18-36 acid glycolester) (available from Croda) and propylene glycol diester waxes including ethylene glycol distearate and glycol distearate. Useful triglyceride waxes include Shea Butter, Cocoa Butter, Synchrowax HGL-C (C18-36 acid triglyceride), Synchrowax HRC (tribehenin), Synchrowax HRS-C [tribehenin (and) calcium behenate] (all available from Croda Inc.), Tristearin, trimyristate and fully hydrogenated vegetable oils and mixtures thereof. Preferred is a mixture of diester and triglyceride waxes in a ratio of from about 5:1 to about 1:1 and more preferably from about 4:1 to about 1:1.

Waxes useful in the compositions of this invention are disclosed in the following, all of which are incorporated by reference herein in their entirety: U.S. Pat. No. 5,219,558 to Woodin, Jr. et al., issued Jun. 15, 1993; U.S. Pat. No. 4,049,792, to Elsnau, issued Sep. 20, 1977; U.S. Pat. No. 4,151,272, to Geary et al., issued Apr. 24, 1975; U.S. Pat. No. 4,229,432, to Geria, issued Oct. 21, 1980; U.S. Pat. No. 4,280,994, to Tumey, issued Jul. 28, 1981; U.S. Pat. No. 4,126,679, to Davy et al., issued Nov. 21, 1978; and European Patent Application Publication Number 117,070 to May, published Aug. 29, 1984, "The Chemistry and Technology of Waxes", A. H. Warth, 2nd Edition, reprinted in 1960, Reinhold Publishing Corporation, pp. 391–393 and 421; "The Petroleum Chemicals Industry", R. F. Goldstein and A. L. Waddeam, 3rd Edition (1967), E & F.N. Span Ltd., pp. 33–40; "The Chemistry and Manufacture of Cosmetics", M. G. DeNavarre, 2nd Edition (1970), Van Nostrand & Company, pp. 354–376; and in "Encyclopedia of Chemical Technology:, Vol. 24, Kirk-Othmer, 3rd Edition (1979) pp. 466–481.

Additional non-limiting examples of useful hardening materials are those selected from the group consisting of sorbitan esters, glyceryl esters, polyglyceryl esters, methyl glucose esters, sucrose esters, ethoxylated fatty alcohols, hydrogenated castor oil ethoxylates, sorbitan ester ethoxylates, polymeric emulsifiers, and silicone emulsifiers.

Sorbitan esters are useful in the present invention. Preferable are sorbitan esters of C16–C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83), sorbitan monoisostearate (e.g., CRILL® 6 made by Croda), sorbitan stearates (e.g., SPAN® 60), sorbitan triooleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Other suitable hardeners for use in the present invention include, but is not limited to, glyceryl monoesters, preferably glyceryl monoesters of C16–C22 saturated, unsaturated and branched chain fatty acids such as glyceryl oleate, glyceryl monostearate, glyceryl monopalmitate, glyceryl monobehenate, and mixtures thereof; polyglyceryl esters of C16–C22 saturated, unsaturated and branched chain fatty acids, such as polyglyceryl-4 isostearate, polyglyceryl-3 oleate, diglycerol monooleate, tetraglycerol monooleate and mixtures thereof; methyl glucose esters, preferably methyl glucose esters of C16–C22 saturated, unsaturated and branched chain fatty acids such as methyl glucose dioleate, methyl glucose sesquiisostearate, and mixtures thereof; sucrose fatty acid esters, preferably sucrose esters of C12–C22 saturated, unsaturated and branched chain fatty acids such as sucrose stearate, sucrose trilaurate, sucrose distearate (e.g., Crodesta® F10), and mixtures thereof; C12–C22 ethoxylated fatty alcohols such as oleth-2, oleth-3, steareth-2, and mixtures thereof, hydrogenated castor oil ethoxylates such as PEG-7 hydrogenated castor oil; sorbitan ester ethoxylates such as PEG-40 sorbitan peroleate, Polysorbate-80, and mixtures thereof; polymeric emulsifiers such as ethoxylated dodecyl glycol copolymer; and silicone emulsifiers such as laurylmethicone copolyol, cetyldimethicone, dimethicone copolyol, and mixtures thereof.

Other useful hardeners include, but is not limited to, phosphatidyl cholines and phosphatidyl choline-containing compositions such as lecithins; long chain C16–C22 fatty acid salts such as sodium stearate; long chain C16–C22 dialiphatic, short chain C1–C4 dialiphatic quaternary ammonium salts such as ditallow dimethyl ammonium chloride and ditallow dimethyl ammonium methylsulfate; long chain C16–C22 dialkoyl(alkenoyl)-2-hydroxyethyl, short chain C1–C4 dialiphatic quaternary ammonium salts such as ditallowoyl-2-hydroxyethyl dimethyl ammonium chloride; the long chain C16–C22 dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate; short chain C1–C4 dialiphatic, long chain C16–C22 monoaliphatic benzyl quaternary ammonium salts such as dimethyl stearyl benzyl ammonium chloride, and synthetic phospholipids such as stearamidopropyl PG-dimonium chloride (Phospholipid PTS from Mona Industries).

Weight Ratios and Weight Percentages

In the present invention, the weight ratio of the lathering surfactant to the conditioning component is less than about 40:7, preferably less than about 5:1, more preferably less than about 2.5:1, and more preferably less than about 1:1.

In certain embodiments of the present invention, the cleansing and conditioning component, which is defined as comprising a lathering surfactant and a conditioning component further comprising an oil soluble conditioning agent and a water soluble conditioning agent, the lathering surfactant comprises from about 1% to about 75%, preferably from about 10% to about 65%, and more preferably from about 15% to about 45%, by weight of the cleansing and conditioning component, and the conditioning component comprises from about 15% to about 99%, preferably from about 20% to about 75%, and more preferably from about 25% to about 55%, by weight of the cleansing and conditioning component.

Additional Ingredients

The compositions which are added onto or impregnated into the articles of the present invention may comprise a wide range of optional ingredients. Some of these ingredients are listed in more detail herein. Particularly useful are added polymers (as distinct from the polymeric material which may form the substrate), various active ingredients, and cationic surfactants useful for delivering various non-conditioning or non-cleansing benefits of the skin or hair during the cleansing and conditioning process.

Polymers

The articles of the present invention may comprise one or more polymers, preferably cationic polymers, nonionic polymers, and mixtures thereof, and more preferably cationic polymers. Such cationic polymers are preferably water dispersible. As used herein, "water dispersible" means that the cationic polymer is either dispersible when the articles described herein are wetted and agitated to produce lather or when the water insoluble substrate is reated with a pre-complex coacervate phase which may be added onto or impregnated into the substrate independently or in combination with either the lathering surfactant or the water-soluble conditioning agent. Complex coacervates of the cationic polymer can be formed with the anionic surfactants of the present articles or with anionic polymers that can optionally be added to the articles hereof (e.g., sodium polystyrene sulfonate). Complex coacervates are believed to more readily deposit water soluble conditioning agents onto the skin or hair. Thus, in general, it is preferred that the cationic polymer exist in/on the articles of the present invention as a complexed coacervate phase or form a coacervate phase upon dilution of the lather produced after wetting and agitating these articles. If the cationic polymer has not already formed a coacervate in or on the articles of the present invention, the polymer will preferably exist in a complex coacervate form upon dilution.

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature. Coacervate systems and the effect of these parameters has previously been studied. See, for example, J. Caelles, et al., "Anionic and Cationic Compounds in Mixed System", Cosmetics Toiletries, Vol. 106, April 1991, pp. 49–54; Van Oss, "Coacervation, Complex-Coacervation and Flocculation", J. Dispersion Science and Technology, Vol. 9 (5,6), 1988–89, pp. 561–573; D. J. Burgess, "Practical Analysis of Complex Coacervate Systems", J. of Colloid and Interface Science, Vol. 140, No. 1, November 1990, pp. 227–238; and U.S. Pat. No. 5,716,920, Glenn Jr. et al., issued Feb. 10, 1998.

Techniques for analysis of formation of complex coacervates are known in the art. For example, microscopic analyses of the lather, at any chosen stage of dilution, can be utilized to identify whether a coacervate phase has formed. Such coacervate phases can be identified as additional emulsified phases and dyes may be useful in distinguishing the coacervate phase from other insoluble phases dispersed in the lather.

Nonlimiting examples of cationic and nonionic polymers useful herein include, but are not limited to, gums, hydrophilic colloids, biological polymers, and proteins and mixtures thereof. Suitable examples of these materials include carboxymethyl hydroxyethylcellulose, carboxymethyl hydroxypropyl guar, carrageenan, cellulose gum, gelatin, guar gum, guar hydroxypropyltrimonium chloride, hydroxyethylcellulose, hydroxypropylcellulose, hydroxypropyl methylcellulose, methylcellulose, xanthan gum, chitin, chitosan, hydroxypropyl chitosan, potato starch, oat protein, milk protein, cocoyl hydrolyzed collagen, cocoyl hydrolyzed keratin, hydroxypropyltrimonium gelatin, and mixtures thereof.

Cellulose derived polymers are also useful herein. By cellulose derived polymers, as used herein, is meant to describe those polymers containing a cellulose backbone, i.e. a polysaccharide backbone of repeating glucose units. In these cellulose derived polymers, the hydroxy groups of the cellulose polymer have been hydroxyalkylated (preferably hydroxyethylated or hydroxypropylated) to form a hydroxyalkylated cellulose which is then further modified with a cationic quaternary ammonium or protonated ammonium group. Preferred cationic modifying groups are those having at least one C10-20 alkyl chain and two shorter alkyl chains (i.e. C1 or C2) on the nitrogen. The substituent on the cellulose polymer can thus be depicted as —(X)NRR'R" wherein X is hydroxyalkyl (preferably—OCH2CH2— or —OCH2CHOHCH2—), R and R' are methyl or ethyl, and R" is C10-20 alkyl [preferably lauryl, stearyl, or cocoyl (i.e. a mixture of alkyl groups derived from coconut oil)]. In other alternative structures it has been found that when R, R', and R" are all methyl (i.e. the trimonium group) that useful cellulose polymers are also obtained. In yet other alternative structures the cationic substituent on the cellulose contains both a hydroxyethyl and a hydroxypropyl group such that the moiety can be depicted as —(OCH2CH2O)—CH2CHOHCH2NRR'R" wherein R, R', and R" are methyl or ethyl, and R" is C10-20 alkyl [preferably lauryl, stearyl, or cocoyl (i.e. a mixture of alkyl groups derived from coconut oil)], or alternatively wherein R, R', and R" are all methyl (i.e. the trimonium group).

Commercially avaialable cationic modified celluloses include: laurdimonium hydroxethyl cellulose (wherein in the above formula X is —OCH2CH2—, R and R' are methyl, and R" is lauryl), steardimonium hydroxyethyl cellulose (wherein in the above formula X is —OCH2CH2—, R and R' are methyl, and R" is stearyl), and cocodimonium hydroxyethyl cellulose (wherein in the above formula X is —OCH2CH2—, R and R' are methyl, and R" is cocoyl). These three materials are known by the trade names Crodacel QL, Crodacel QS, and Crodacel QM, respectively, which are all commercially available from Croda Corp. Another highly useful cationic cellulose is laurdimmonium hydroxypropyl oxyethyl cellulose (wherein the modifying group on the cellulose is —(OCH2CH2O)—CH2CHOHCH2NRR'R", wherein R R' are methyl and R" is lauryl), which is commercially available as Crodacel QL Special, from Croda Corp. Other useful cationic celluloses are available from Amerchol Corp. (Edison, N.J., USA) in their Polymer JRTN, LRTN, and LKFN series of polymers, as salts of hydroxyethyl cellulose reacted with trimethyl ammonium substituted epoxide, referred to in the industry (CTFA) as Polyquaternium 10; cationic cellulose ethers described in U.S. Pat. Nos. 3,816,616 4,272,515, which are commercially available from Union Carbide Corp. under the trademark Polymer Jr.; and the polymeric quaternary ammonium salts of hydroxyethyl cellulose reacted with lauryl dimethyl ammonium-substituted epoxide, referred to in the industry (CTFA) as Polyquaternium 24 which are available from Amerchol Corp. (Edison, N.J., USA) under the tradename Polymer LM-200.

Other suitable cationic polymers that can be used herein include cationic guar gum derivatives, such as the cationic polygalactomannan gum derivative described in U.S. Pat. No. 4,298,494 which are commercially available under the trademark JAGUAR; the hydroxypropyltrimethylammonium derivative of guar gum which is commercially available under the trademark JAGUAR C-13-S and JAGUAR C-17 (CTFA designation guar hydroxypropyltrimonium chloride); and the hydroxypropylated cationic guar derivative known as JAGUAR C-16 (commercially available from Celanese Corp. in their Jaguare series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein). Especially preferred cationic polymers include Polyquatemium 10.

Related to these cellulose polymers are ones having backbones that are derived from other sugars (or their related acids, alcohols, amines, etc.), e.g. galactose, mannose, arabinose, xylose, fucose, fructose, glucosamine, galactosamine, glucuronic acid, galacturonic acid, 5 or 6 membered ring polyalcohols, and mixtures thereof.

Protein derived polymers are another type of useful derivative of a naturally occuring polymer. The protein derived polymers useful herein are derived from a wide variety of protein sources. However, those that are derived from hydrolyzed proteins (i.e., proteins which are broken down into lower molecular weight segements of from about 1000 MW to about 5000 MW) are preferred. Hydrolyzed proteins are well known to the cosmetic chemist of ordinary skill in the art and can be derived using standard synthetic techniques such as the acid, alkaline, or enzymatic hydrolysis of various protein sources. The protein source used will determine the ultimate amino acid composition of the hydrolzyed protein obtained. Nonlimiting examples of hydrolyzed proteins which are useful as polymers herein include those selected from the group consisting of hydrolyzed casein, hydrolyzed collagen, hydrolyzed conchiorin protein, hydrolyzed corn protein, hydrolyzed elastin, hydrolyzed fibronectin, hydrolyzed hair keratin, hydrolyzed human placental protein, hydrozlyed keratin, hydrolyzed potato protein, hydrolyzed rice protein, hydrolyzed silk, hydrolyzed soy protein, hydrolyzed vegetable protein, hydrolyzed wool protein, hydrolyzed wheat protein, and mixtures thereof. These hydrolyzed proteins are described in the CTFA International Cosmetic Ingredient Dictionary, 1991, pp. 246–249, which are incorporated by reference herein in their entirety.

It has been found that cationically modified hydrolyzed proteins are especially useful polymers in the present invention. Using a variety of synthetic techniques known to the artisan of ordinary skill in the chemical arts, the nitrogen atoms of the amino acids comprising these hydrolyzed proteins can be hydroxyalkylated (preferably hydroxyethylated or hydroxypropylated) to form a hydroxyalkylated protein hydrolyzate which is then further modified with a cationic quaternary ammonium or protonated ammonium group. Preferred cationic modifying groups are those having at least one C10-20 alkyl chain and two shorter alkyl chains (i.e. C1 or C2) on the nitrogen. The substituent on the hydrolyzed protein can be depicted as —(X)NRR'R" wherein X is hydroxyalkyl (preferably—OCH2CH2— or —OCH2CHOHCH2—), R and R' are methyl or ethyl, and R" is C10-20 alkyl [(preferably lauryl, stearyl, or cocoyl (i.e. a mixture of alkyl groups derived from coconut fats)]. In other alternative structures it has been found that when R, R', and R" are all methyl (i.e. the trimonium group) that useful cationic hydrolyzed proteins are also obtained. Commercially avaialable cationic modified protein hydrolyzates include: hydroxypropyltrimonium hydrolyzed casein, hydroxypropyltrimonium hydrozlyed collagen, hydoxypropyltrimonium hydrolyzed keratin, hydroxypropyltrimonium hydrolyzed silk, hydroxypropyl trimonium hydrolyzed soy protein, hydroxypropyl trimonium hydrolyzed vegetable protein, and hydroxypropyltrimonium hydroylzed wheat protein, wherein the —(X)NRR'R" substituent on each of these protein hydrolyzates is such that X is —OCH2CHOHCH2—, and R, R', and R" are methyl. These hydrolyzed proteins are described in the CTFA International Cosmetic Ingredient Dictionary, 1991, pp. 254–255, which are incorporated by reference herein in their entirety. Other commercially avaialable cationic modified protein hydrolyzates include lauryldimonium hydroxypropyl hydrolyzed collagen, lauryldimonium hydroxypropyl hydrolyzed keratin, lauryldimonium hydroxypropyl hydrolyzed silk, lauryldimonium hydroxypropyl hydrolyzed soy protein, stearyldimonium hydroxypropyl hydrolyzed casein, stearyldimonium hydroxypropyl hydrolyzed collagen, stearyldimonium hydroxypropyl hydrolyzed keratin, stearyldimonium hydroxypropyl hydrolyzed rice protein, stearyldimonium hydorxypropyl hydrolyzed silk, stearyldimonium hydroxypropyl hydrolyzed vegetable protein, stearyldimonium hydroxypropyl hydrolyzed wheat protein, cocodimonium hydroxypropyl hydrolyzed casein, cocodimonium hydroxypropyl hydrolyzed collagen, cocodimonium hydroxypropyl hydrolyzed keratin, cocodimonium hydroxypropyl hydrolyzed rice protein, cocodimonium hydroxypropyl hydrolyzed silk, cocodimonium hydroxypropyl hydrolyzed soy protein, cocodimnoium hydroxypropyl hydrolyzed wheat protein, wherein in each of these protein hydrolyzates the —(X)NRR'R" substituent is such that X is —OCH2CHOHCH2—, R and R' are methyl, and R" is lauryl or stearyl or cocoyl. These hydrolyzed proteins are described in the CTFA International Cosmetic Ingredient Dictionary, 1991, pp. 112–113, 293–294, 586, which are incorporated by reference herein in their entirety. Preferred among these cationic hydrolyzed proteins are lauryldimmonium hydroxypropyl hydrolyzed collagen, lauryldimmonium hydroxypropyl hydrolyzed kderatin, lauryldimmonium hydroxypropyl hydrolyzed keratin, lauryldimmonium hydroxypropyl hydrolyzed silk, lauryldimmonium hydroxypropyl hydrolyzed soy protein, and mixtures thereof.

Polymeric ethers are also useful herein. These materials are also known as polyethylene glycols and polypropylene glycols (designated as PEG and PPG in the CTFA, respectively). Nonlimiting examples of these materials include PEG 2M, PEG 7M, PEG 14M, PEG 25M, PEG 75, PEG 90, PEG 100, and mixtures thereof.

Synthetic cationic polymers and copolymers are also useful herein. Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have C1–C7 alkyl groups, more preferably C1–C3 alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quatemized subsequent to formation of the polymer. For example, tertiary amine functionalities can be quatemized by reaction with a salt of the formula R'X wherein R' is a short chain alkyl, preferably a C1–C7 alkyl, more preferably a C1–C3 alkyl, and X is an anion which forms a water soluble salt with the quatemized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quatemized pyrrolidone, e.g., alkyl vinyl imidazolium, alkyl vinyl pyridinium, alkyl vinyl pyrrolidone salts. The alkyl portions of these monomers are preferably lower alkyls such as the C1–C3 alkyls, more preferably C1 and C2 alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably C1–C7 hydrocarbyls, more preferably C1–C3, alkyls.

The cationic polymers hereof can comprise mixtures of monomer units derived from amine- and/or quaternary ammonium-substituted monomer and/or compatible spacer monomers.

Suitable synthetic cationic polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquatemium-16), such as those commercially available from BASF Wyandotte Corp. (Parsippany, N.J., USA) under the Luviquat tradename (e.g., Luviquat FC 370); copolymers of 1-vinyl-2-pyrrolidone and dimethylaminoethyl methacrylate (referred to in the industry by CTFA as Polyquaternium-11) such as those described in U.S. Pat. No. 4,080,310 and commercially available from ISP Corporation (Wayne, N.J., USA) under the Gafquat tradename (e.g., Gafquat 755 and 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquatemium 6 and Polyquatemium 7, respectively; the mineral acid salts of amino-alkyl esters of homo- and co-polymers of unsaturated carboxylic acids having from 3 to 5 carbon atoms, as described in U.S. Pat. No. 4,009,256; the graft cationic copolymer containing N-vinylpyrrolidone, dimethylaminoethyl methacrylate and polyethylene glycol described in U.S. Pat. No. 4,048,301; the polymers of etherified starch described in U.S. Pat. No. 3,186,911; cationic polyacrylamides of the type described in British Pat. App. 94031565.4; the high molecular weight cationic polymers designated in the CTFA as Quatemium-40 (a highly charged cationic dimethyldiallylammonium chloride homopolymer) and Quaternium-41 (a highly charged cationic copolymer prepared with dimethyldiallylammonium chloride and acrylamide), which are commercially available under the trademarks Merquat 100 and Merquat 550 from Merck & Co., Inc.; and mixtures thereof. Further nonlimiting examples of other suitable synthetic polymers include acrylylates/C10-30 alkyl acrylate crosspolymer, acrylates copolymer, acrylates/PVP copolymer, acrylates/VA copolymer, butylated polyoxymethylene urea, butylated PVP, carbomer, hydroxyethyl PEI-1000, methyl methacrylate crosspolymer, PEI-1000, PEI-1500, PEI-2500, polybutene, polyacrylamide, polyacrylic acid, polyethylene, polyisobutene, polymethyl methacrylate, polyquaternium (1–44), polystyrene, polyvinly alcohol, PVP, PVP/Eicosene copolymer, PVP/VA copolymer, sodium acrylates copolymer, sodium carbomer, sodium polyacrylate, sodium polymethacrylate, styrene/PVP copolymer, TEA carbomer, and mixtures thereof.

Other useful water soluble polymers include polyvinylpyrrolidone and copolymers of vinylpyrrolidone such as those containing vinyl acetate, dimethylaminoethylmethacrylate and quaternary versions of the same with methyl sulfates, and polymers and copolymers of vinyl alcohol and vinyl acetate. Another highly useful polymer is the protonated form of polyethyleneimine. Polyethylenimine is a polymer which is produced from the polymerization of ethylenimine. The protonated polyethylenimine polymers preferred herein are those having a molecular weight of from about 500,000 to about 750,000, branching such that the ratio of primary to secondary to tertiary nitrogen is about 1:2:1, a tertiary nitrogen site on average at about every 3 to about 3.5 atoms, a charge density of about 20 miliequizalvents per gram at pH 4.5, a density of about 1070 kg/m$^3$, and a viscosity of about 17,000 to about 28,000 milli-Pascals. A protonated polyethylenimine polymer meeting this description is commercially avaialable as Polymin P from BASF Corp.

Among the cationic polymers useful herein, preferred are those selected from the group consisting of hydroxyethyl cellulose, hydroxypropyl cellulose, lauryldimmonium hydroxypropyl oxyethyl cellulose, laurdimonium hydroxyethyl cellulose, steardimonium hydroxyethyl cellullose, cocodimonium hydroxyethyl cellulose, hydroxypropyl hydrolyzed collagen, lauryldimmonium hydroxypropyl hydrolyzed keratin, lauryldimmonium hydroxypropyl hydrolyzed keratin, lauryldimmonium hydroxypropyl hydrolyzed silk, lauryldimmonium hydroxypropyl hydrolyzed soy protein, protonated polyethylenimine, polyquaternium 10, and mixtures thereof. More preferred are lauryldimonium hydroxypropyl hydrolyzed collagen, laurdimonium hydroxypropyl oxyethyl cellulose, and mixtures thereof. Preferably the deposition aid is selected from the group comprising hydroxyalkyl cellulose ethers and cationic guar derivatives. Particularly preferred deposition aids are Jaguar C13S with a cationic charge density of 0.8 meq/g. Other particularly preferred materials include Jaguar C15, Jaguar C17, Jaguar C16, Jaguar C162, polyquaternium 10, and mixtures thereof. Most preferred is polyquaternium 10 (e.g., Polymer JR400 and Polymer JR30M).

Among the nonionic polymers useful herein, preferred are those selected from the group consisting of hydrolyzed casein, hydrolyzed collagen, hydrolyzed vegetable protein, guar gum, polyvinylpyrrolidone, PEG 14M, and mixtures thereof. More preferred is PEG 14M and hydrolized casein.

Active Ingredients

The articles of the present invention can optionally comprise a safe and effective amount of one or more active ingredients or pharmaceutically-acceptable salts thereof.

The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medical judgment. What is a safe and effective amount of the active ingredient will vary with the specific active, the ability of the active to penetrate through the skin, the age, health condition, and skin condition of the user, and other like factors.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically-acceptable salts of these active ingredients are useful herein. The following active ingredients are useful in the compositions of the present invention.

Anti-Acne Actives:

Examples of useful anti-acne actives include the keratolytics such as salicylic acid (o-hydroxybenzoic acid), derivatives of salicylic acid such as 5-octanoyl salicylic acid and 4-methoxylsalicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids and bioflavonoids; and bile salts such as scymnol sulfate and its derivatives, deoxycholate, and cholate; abietic acid; adapalene; allantoin; aloe extracts; arbietic acid and its salts; ASEBIOL (available from Laboratories Serobiologiques, located in Somerville, N.J.); azaleic acid; barberry extracts; bearberry extracts; belamcanda chinensis; benzoquinolinones; berberine; BIODERMINE (available from Sederma, located in Brooklyn, N.Y.); bisabolol; S-carboxymethyl cysteine; carrot extracts; cassin oil; clove extracts; citral; citronellal; CREMOGEN M82 (available from Dragoco, located in Totowa, N.J.); cucumber extracts; dehydroacetic acid and its salts; dehydroeplandersterone salicylate; dichlorophenyl imidazoldioxolan which is commercially available as COMPLETECH MBAC-OS (from Lipo, located in Paterson, N.J.); DL valine and its esters; DMDM hydantoin; erythromycin; escinol; ethyl hexyl monoglyceryl ether; ethyl 2-hydroxy undecanoate; farnesol; farnesol acetate; geranoil; glabridin; gluconic acid; gluconolactone; glyceryl monocaprate; glycolic acid; grapefruit seed extract; gugu lipid; hesperitin; hinokitol; hops extract; hydrogenated rosin; 10 hydroxy decanoic acid; ichtyhol; interleukin 1 alpha antagonists; ketoconazole; lactic acid; lemon grass oil; linoleic acid; LIPACIDE C8CO (available from Seppic, located in Paris, France); lovastatin; metronidazole; minocycline; mukurossi; neem seed oil; vitamin B3 compounds (such as niaincamide and nicotinic acid); nisin; octopirox; panthenol; 1-pentadecanol; peonia extract; peppermint extract; phelladendron extract; 2-phenyl-benzothiophene derivatives; phloretin; PHLOROGINE (available from Secma); phosphatidyl choline; proteolytic enzymes; quercetin; red sandalwood extract; rosemary extract; rutin; sage extract; skull cap extract; siber hegner extract; siberian saxifrage extract; silicol; sodium lauryl sulfate; sodium sulfoacetamide; sorbic acid; sulfur; sunder vati extract; tea tree oil; tetracyline; tetra hydroabietic acid; thyme extract; tioxolone; tocopherol; trehalose 6-undecylenoate; 3 tridecene-2-ol; tropolone; UNITRIENOL T27 (available from Unichem, located in Gouda, Netherlands); vitamin D3 and its analogs; white thyme oil; wogonin; Ylang Ylang; zinc glycerolate; zinc linoleate; zinc oxide; zinc pyrithione; zinc sulfate and mixtures thereof.

Anti-Wrinkle and Anti-Skin Atrophy Actives:

Examples of antiwrinkle and anti-skin atrophy actives include retinoic acid and its derivatives (e.g., cis and trans); retinol; retinal; retinyl esters (e.g., retinyl acetate, retinyl palmitate, and retinyl proprionate); vitamine B3 compounds (such as niacinamide and nicotinic acid), salicylic acid and derivatives thereof (e.g., 5-octanoyl salicylic acid, heptyloxy-4-salicylic acid, and 4-methoxy salicylic acid); sulfur-containing D and L amino acids and their derivatives and salts, particularly the N-acetyl derivatives, a preferred example of which is N-acetyl-L-cysteine; thiols, e.g. ethane thiol; hydroxy acids, phytic acid, lipoic acid; lysophosphatidic acid, and skin peel agents (e.g., phenol and the like); adapalene; ademethionine; adenosine; aletris extract; aloe derived lectins; 3-aminopropyl dihydrogen phosphate; anise extracts; AOSINE (available from Secma); ASC III (available from E. Merck, located in Darmstadt, Germany); ascorbic acid; ascorbyl palmitate; asiatic acid; asiaticosides; ARLAMOL GEO™ (available from ICI, located in Wilmington, Del.); azaleic acid; benzoic acid derivatives; bertholletia extracts; betulinic acid; BIOCHANIN A AND BIOPEPTIDE CL, (available from Sederma, located in Brooklyn, N.Y.); BIOPEPTIDE EL (available from Sederma); blackberry bark extract; blackberry lily extracts; black cohosh extract; butanoyl betulinic acid; citric acid esters; chaste tree extract; clover extracts; daidzein; debromo laurinterol; 1-decanoyl-glycero-phosphonic acid; dehydrocholesterol; dehydrodicreosol; dehydrodicugenol;

dehydroepiandersterone; DERMOLECTINE (available from Sederma); dehydroascorbic acid; dehydroepiandersterone sulfate; dianethole; 2,4 dihydroxybenzoic acid; diosgenin; disodium ascorbyl phosphate; dodecanedioic acid; estrogen and its derivatives; ethocyn; ELESERYL SH (available from Laboratories Serobiologiques, located in Somerville, N.J.); ENDONUCLEINE (available from Laboratories Serobiologiques); ergosterol; eythrobic acid; fennel extract; fenugreek seed extract; FIBRASTIL (available from Sederma); FIBROSTIMULINES S and P (available from Sederma); FIRMOGEN LS 8445 (available from Laboratories Serobiologiques); formononetin; forsythia fruit extract; gallic acid esters; gamma butyric acid; GATULINE RC (available from Gattlefosse, located in Priest, France); genistein; genisteine; genistic acid; gingko bilboa extracts; ginseng extracts; ginsenoside (RO, R6-1, R6-2,R6-3, RC, RD, RE, RF, RF-2, RG-1, RG-2); gluco pyranosyl-1-ascorbate; glutathione and its esters; hexahydro curcumin; HMG-coenzyme A reductase inhibitors; hops extracts; 11 hydroxy undecanoic acid; 10 hydroxy decanoic acid; 25-hydroxycholesterol; kinetin; L-2-OXO-thiazolidine-4-carboxylic acid esters; lactate dehydrogenase inhibitors; 1-lauryl; -lyso-phosphatidyl choline; licorice extracts; lumisterol; luteolin; magnesium ascorbyl phosphate; melatonin; metalloproteinase inhibitors; methoprene; methoprenic acid; MPC COMPLEX (available from CLR); N methyl serine; N methyl taurine; N,N1-bis (lactyl) cystcamine; naringenin; neotigogenin; oleanolic acid; photoanethone; placental extracts; pratensein; pregnenolone; pregnenolone acetate; pregnenolone succinate; premarin; raloxifene; REPAIR FACTOR 1 and REPAIR FACTOR FCP (both available from Sederma); retinoates (esters of C2–C20 alcohols); retinyl glucuronate; retinyl linolcate; S-carboxymethyl cysteine; SEANAMINE FP (available from Laboratories Serobiologiques); soya extracts; spleen extracts; tachysterol; tazarotene; thymulen; thymus extracts; tigogenin; tocopheryl retinoate; traumatic acid; tricholine citrate; trifoside; ursolic acid; vitamin D3 and its analogs; yam extract; yamogenin; zeatin; and mixtures thereof.

Skin Barrier Repair Actives:

Skin barrier repair actives are those skin care actives which can help repair and replenish the natural moisture barrier function of the epidermis. Nonlimiting examples of skin barrier repair actives include brassicasterol; caffeine; campesterol; canola derived sterols; CERAMAX (available from Quest, located in Ashford, England); CERAMIDE 2 and CERAMIDE HO3™ (both available from Sederma); CERAMIDE II and CERAMIDE III (both available from Quest); IIIB (available from Cosmoferm, located in Deft, Netherlands); CERAMIDE LS 3773 (available from Laboratories Serobiologiques); CERAMINOL (available from Inocosm); cholesterol; cholesterol hydroxystearate; cholesterol isostearate; 7 dehydrocholesterol; DERMATEIN BRC and DERMATEIN GSL (both available from Hormel); ELDEW CL 301 AND ELDEW PS 203 (both available from Ajinomoto); glyceryl serine amide; lactic acid; lanolin alcohols; lanosterol; lauric acid N laurylglucamide; lipoic acid; N-acetyl cysteine; N-acetyl-L-serine; N methyl-L-Serine; vitamin B3 compounds (such as niacinamide and nicotinic acid); palmitic acid; panthenol; panthetine; phosphodiesterase inhibitors; PHYTO/CER (available from Intergen); phytoglycolipid millet extract (available from Barnet Products Distributer, located in Englewood, N.J.); PHYTOSPH-INGOSINE (available from Gist Brocades, located in King of Prussia, Pa.); PSENDOFILAGGRIN (available from Brooks Industries, located in South Plainfield, N.J.); QUESTAMIDE H (available from Quest); serine; sigmasterol; sitosterol; soybean derived sterols; sphingosine; S-lactoyl glutathione; stearic acid; SUPER STEROL ESTERS (available from Croda); thioctic acid; THSC CERAMIDE OIL (available from Campo Research); trimethyl glycine; tocopheryl nicotinate; vitamin D3; Y2 (available from Ocean Pharmaceutical); and mixtures thereof.

Non-steroidal Cosmetic Soothing Actives:

Cosmetic soothing actives can be effective in preventing or treating inflammation of the skin. The soothing active enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency. Nonlimiting examples of cosmetic soothing agents include the following categories: propionic acid derivatives; acetic acid derivatives; fenamic acid derivatives; biphenylcarboxylic acid derivatives; and oxicams. All of these cosmetic soothing actives are fully described in U.S. Pat. No. 4,985,459 to Sunshine et al., issued Jan. 15, 1991, incorporated by reference herein in its entirety. Nonlimiting examples of useful cosmetic soothing actives include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, absinthium, acacia, aesc in, alder buckthorn extract, allantoin, aloe, aloe, APT (avaiable from Centerchem), arnica, astragalus, astragalus root extract, azulene, baikal skullcap, baizhu, balsam canada, bee pollen, BIOPHYTEX (avaiable from Laboratories Serobiologiques), bisabolol, black cohosh, black cohosh extract, blue cohosh, blue cohosh extract, boneset, borage, borage oil, bromelain, calendula, calendula extract, candelilla wax, Cangzhu, canola phytosterols, capsicum, carboxypeptidase, celery seed, celery stem extract, CENTAURIUM (avaiable from Sederma), centaury extract, chamazulene, chamomile, chamomile extract, chaparral, chaste tree, chaste tree extract, chickweed, chicory root, chicory root extract, chirata, chishao, collodial oatmeal, comfrey, comfrey extract, CROMOIST CM GLUCAN (avaiable from Croda), dehurian angelica, devil's claw, divalent metals (such as, magnesium, strontium, and manganese), doggrass, dogwood, eleuthero, ELHIBIN (avaiable from Pentapharm), ENTELINE 2 (avaiable from Seema), ephedra, epimedium, evening primrose, eyebright, Fangfeng, feverfew, ficin, forsythia fruit, ganoderma, gaoben, gentian, germanium extract, gingko bilboa, ginkgo, ginseng extract, goldenseal, gorgonian extract, gotu kola, grape fruit extract, guaiac wood oil, guggal extract, helenalin esters, henna, honeysuckle flower, horehound extract, horsechestnut, horsetail, huzhang, hypericum, ichthyol, immortelle, ipecac, job's tears, jujube, kola extract, LANACHRYS 28 (avaiable from Lana Tech), lemon oil, lianqiao, licorice root, ligusticum, ligustrum, lovage root, luffa, mace, magnolia flower, manjistha extract, margaspidin, margaspidin, matricin, MICROAT IRC (avaiable from Nurture), mints, mistletoe, musk, oat extract, orange, panthenol, papain, peony bark, peony root, purslane, QUENCH T (avaiable from Centerchem), quillaia, red sage, rehmannia, rhubarb, rosemary, rosmarinic acid, royal jelly, rue, rutin, sandlewood, sanqi, sarsaparilla, saw palmetto, SENSILINE (avaiable from Silab), SIEGESBECKIA (avaiable from Sederma), stearyl glycyrrhetinate, storax, sweet birch oil, sweet woodruff, tagetes, tea extract, thyme extract, tienchi ginseng, tocopherol, tocopheryl acetate, turmeric, urimel, ursolic acid, white pine bark, witch hazel, xinyi, yarrow, yeast extract, yucca, and mixtures thereof.

Non-Steroidal Anti-Inflammatory Actives (NSAIDS):

Examples of NSAIDS include the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al., issued Jan. 15, 1991, incorporated by reference herein in its entirety. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics:

Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial Tanning Agents and Accelerators:

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; acetyl tyrosine; phospho-DOPA; brazilin; caffeine; coffee extracts; dihydroxyacetone; DNA fragments; isobutyl methyl xanthine; methyl xanthine; prostaglandins; tea extracts; theophylline; UNIPERTAN P2002 and UNIPERTAN P27 (both avaiable from Unichem); and mixtures thereof.

Skin Lightening Actives:

Skin lightening actives can actual decrease in the amount of melanin in the skin or an such an effect by other mechanisms. Skin lightening actives suitable for use herein are described in copending patent application Ser. No. 08/479,935, filed on Jun. 7, 1995 in the name of Hillebrand, corresponding to PCT Application No. U.S. 95/07432, filed Jun. 12, 1995; and copending patent application Serial No. 08/390,152, filed on Feb. 24, 1995 in the names of Kalla L. Kvalnes, Mitchell A. DeLong, Barton J. Bradbury, Curtis B. Motley, and John D. Carter, corresponding to PCT Application No. U.S. 95/02809, filed Mar. 1, 1995, published Sep. 8, 1995; all incorporated herein by reference. Nonlimiting examples of skin lightening actives useful herein include adapalene, aloe extract, ammonium lactate, anethole derivatives, apple extract, arbutin, ascorbic acid, ascorbyl palmitate, azelaic acid, bamboo extract, bearberry extract, bletilla tuber, bupleurum falcatum extract, burnet extract, butyl hydroxy anisole, butyl hydroxy toluene, Chuanxiong, Dang-Gui, deoxyarbutin, 1,3 diphenyl propane derivatives, 2,5 dihydroxybenzoic acid and its derivatives, 2-(4-acetoxyphenyl)-1,3 dithane, 2-(4-hydroxyphenyl)-1,3 dithane, ellagic acid, escinol, estragole derivatives, FADE-OUT (available from Pentapharm), Fangfeng, fennel extract, ganoderma extract, gaoben, GATULINE WHITENING (available from Gattlefosse), genistic acid and its derivatives, glabridin and its derivatives, gluco pyranosyl-1-ascorbate, gluconic acid, glycolic acid, green tea extract, 4-Hydroxy-5-methyl-3[2H]-furanone, hydroquinone, 4 hydroxyanisole and its derivatives, 4-hydroxy benzoic acid derivatives, hydroxycaprylic acid, inositol ascorbate, kojic acid, lactic acid, lemon extract, linoleic acid, magnesium ascorbyl phosphate, MELAWHITE (available from Pentapharm), morus alba extract, mulberry root extract, niacinamide, 5-octanoyl salicylic acid, parsley extract, phellinus linteus extract, pyrogallol derivatives, retinoic acid, retinol, retinyl esters (acetate, propionate, palmitate, linoleate), 2,4 resorcinol derivatives, 3,5 resorcinol derivatives, rose fruit extract, salicylic acid, Song-Yi extract, 3,4,5 trihydroxybenzyl derivatives, tranexamic acid, vitamin D3 and its anaologs, and mixtures thereof.

Sebum Stimulators:

Sebum stimulators can increase the production of sebum by the sebaceous glands. These skin care actives are especially useful for post menopausal women who are sebum deficient. Nonlimiting examples of sebum stimulating actives include bryonolic acid, dehydroetiandrosterone (also known as DHEA), orizanol and mixtures thereof.

Sebum Inhibitors:

Sebum inhibitors can decrease the production of sebum by the sebaceous glands. Nonlimiting examples of sebum inhibiting actives include ASEBIOL (available from Laboratories Serobiologiques), BIODERMINE (available from Sederma), COMPLETECH MBAC-OS (available from Lipo), cucumber extracts, dehydroacetic acid and its salts, dichlorophenyl imidazoldioxolan, niacinamide, phloretin, PHLOROGINE (available from Secma), S-carboxylmethyl cysteine, tioxolone, tocopherol, UNITRIENOL T27 (available from Unichem), and mixtures thereof.

Antimicrobial and Antifungal Actives:

Examples of antimicrobial and antifungal actives include B-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxypropanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole; alantolactone; isoalantolactone; alkanet extract (alaninin); anise; arnica extract (helenalin acetate and 11,13 dihydrohelenalin); Aspidium extract (phloro, lucinol containing extract); barberry extract (berberine chloride); bay sweet extract; bayberry bark extract (myricitrin); benzalkonium chloride; benzethonium chloride; benzoic acid and its salts; benzoin; benzyl alcohol; blessed thistle; bletilla tuber; bloodroot; bois de rose oil; burdock; butyl paraben; cade oil; CAE (available from Ajinomoto, located in Teaneck, N.J.); cajeput oil; Cangzhu; caraway oil; cascarilla bark (sold under the tradename ESSENTIAL OIL); cedarleaf oil; chamomille; chaparral; chlorhexidine gluconate; chlorophenesin; chlorxylenol; cinnamon oil; citronella oil; clove oil; dehydroacetic acid and its salts; dill seed oil; DOWICIL 200 (available from Dow Chemical, located in Midland, Mich.); echinacea; elenolic acid; epimedium; ethyl paraben; Fo-Ti;

galbanum; garden burnet; GERMALL 115 and GERMALL II (available from ISP-Sutton Labs, located in Wayne, N.J.); German chamomile oil; giant knotweed; GLYDANT (available from Lonza, located in Fairlawn, N.J.); GLYDANT PLUS (available from Lonza); grapefruit seed oil; hexamidine diisethionate; hinokitiol; honey; honeysuckle flower; hops; immortelle; iodopropynl butyl carbamide (available from Lonza); isobutyl paraben; isopropyl paraben; JM ACTICARE (available from Microbial Systems International, located in Nottingham, NG); juniper berries; KATHON CG (available from Rohm and Haas, located in Philadelphia, Pa.); labdanum; lavender; lemon balm oil; lemon grass; methyl paraben; mint; mume; mustard; myrrh; neem seed oil; ortho phenyl phenol; olive leaf; parsley; patchouly oil; peony root; PHENONIP (available from Nipa Labs, located in Wilmington, Del.); phenoxyethanol; pine needle oil; PILANSERVATIVE (available from Campo Research); propyl paraben; purslane; quillaira; rhubarb; rose geranium oil; rosemary; sage; salicylic acid; sassafras; savory; sichuan lovage; sodium meta bisulfite; sodium sulfite; SOPHOLIANCE (available from Soliance, located in Compiegne, France); sorbic acid and its salts; stevia; storax; tannic acid; tea; tea tree oil (cajeput oil); thyme; triclosan; triclocarban; tropolone; turpentine; umbelliferone (antifungal); yucca; zinc pyrithione; and mixtures thereof.

Sunscreen Actives:

Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof. Exact amounts of sunscreens which can be employed will vary depending upon the sunscreen chosen and the desired Sun Protection Factor (SPF) to be achieved. SPF is a commonly used measure of photoprotection of a sunscreen against erythema. See Federal Register, Vol. 43, No. 166, pp. 38206–38269, Aug. 25, 1978, which is incorporated herein by reference in its entirety.

Preferred examples of actives useful herein include those selected from the group consisting of salicylic acid, benzoyl peroxide, 3-hydroxy benzoic acid, glycolic acid, lactic acid, 4-hydroxy benzoic acid, acetyl salicylic acid, niacinamide, cis-retinoic acid, trans-retinoic acid, retinol, retinyl palmitate, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, 2-ethylhexyl p-methoxycinnamic acid, oxybenzone, 2-phenylbenzimidozole-5-sulfonic acid, dihydroxyacetone, panthenol, lactic acid, arbutin, kojic acid, allantoin, cholesterol, C10–C30 cholesterol/lanosterol esters, tocopherol, tocopheryl acetate, and mixtures thereof.

Cationic Surfactants

The articles of the present invention can also optionally comprise one or more cationic surfactants, provided these materials are selected so as not to interfere with the overall lathering characteristics of the required, lathering surfactants. Cationic surfactants are useful as anti-static agents or as emulsifiers.

Nonlimiting examples of cationic surfactants useful herein are disclosed in McCutcheon's, Detergents and Emulsifiers, North American edition (1986), published by allured Publishing Corporation; and McCutcheon's, Functional Materials, North American Edition (1992); both of which are incorporated by reference herein in their entirety.

Nonlimiting examples of cationic surfactants useful herein include cationic alkyl ammonium salts such as those having the formula:

R1R2R3R4N+X− wherein R1, is selected from an alkyl group having from about 12 to about 18 carbon atoms, or aromatic, aryl or alkaryl groups having from about 12 to about 18 carbon atoms; R2, R3, and R4 are independently selected from hydrogen, an alkyl group having from about 1 to about 18 carbon atoms, or aromatic, aryl or alkaryl groups having from about 12 to about 18 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, R1 is an alkyl group having from about 12 to about 18 carbon atoms; R2 is selected from H or an alkyl group having from about 1 to about 18 carbon atoms; R3 and R4 are independently selected from H or an alkyl group having from about 1 to about 3 carbon atoms; and X is as described in the previous paragraph.

Most preferably, R1 is an alkyl group having from about 12 to about 18 carbon atoms; R2, R3, and R4 are selected from H or an alkyl group having from about 1 to about 3 carbon atoms; and X is as described previously.

Alternatively, other useful cationic surfactants include amino-amides, wherein in the above structure R1 is alternatively R5CO—(CH2)n,—, wherein R5 is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

Other Optional Ingredients

The articles of the present invention can comprise a wide range of other optional components. These additional components should be pharmaceutically acceptable. The CTFA Cosmetic Ingredient Handbook, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these and other functional classes include: abrasives, absorbents, anticaking agents, antioxidants, vitamins, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, and sunscreening agents.

Also useful herein are aesthetic components such as fragrances, pigments, colorings, essential oils, skin sensates, astringents, skin soothing agents, and skin healing agents.

Methods of Manufacture

The disposable, single use personal care cleansing and conditioning articles of the present invention are manufactured by separately or simultaneously adding onto or impregnating into a water insoluble substrate having at least a wet extensible portion a lathering surfactant and a conditioning component, wherein said resulting article is substantially dry. By "separately" is meant that the surfactants and conditioning agents can be added sequentially, in any order without first being combined together. By "simultaneously" is meant that the surfactants and conditioning agents can be added at the same time, with or without first being combined together. The lathering surfactant and/or the conditioning component can also be added onto or impregnated into either layers (100 or 200) in any sequence. Alternatively, the lathering surfactant and/or the conditioning component can be added onto or impregnated into the resulting combination of the first layer 100 and the second layer 200. Treatment with the lather surfactant and/or the conditioning component can be achieved at anytime before or after joining the first layer 100 and the second layer 200. Despite the order of treatment, excess surfactant and/or conditioning component should be removed (e.g., by a nipping process). Thereafter, the treated material (e.g., the first layer 100, the second layer 200, both layers 100 and 200, or joined substrate) should be dried by conventional means.

For example, prior to joining the first layer 100 to the second layer 200, the second second layer can be treated with the lathering surfactant. After joining the two layers, either of the outside surfaces (e.g., the unjoined surfaces) of layers 100 and/or 200 can be treated with the conditioning component. Alternatively, the lathering surfactants and conditioning agents can be added onto or impregnated into the second layer 200 at the same time prior to joining the two layers. Alternatively, the lathering surfactants and the conditioning agents can be combined together before adding onto or impregnating into the second layer 200.

Alternatively, prior to joining the two layers, the first layer 100 can be treated with the lathering surfactant employing methods which do not cause the first layer to elongate or extend. This can be achieved in the manufacturing of the first layer or by various application methods well known to those of ordinary skill in the art. Nonlimiting examples of application methods include extrusion coating and slot coating.

The surfactant, conditioning agents, and any optional ingredients can be added onto or impregnated into either layer (100 or 200) or the resulting joined layers (100 and 200) by any means known to those skilled in the art: for example, by spraying, laser printing, splashing, dipping, soaking, or coating.

When water or moisture is used or present in the manufacturing process, the resulting treated substrate is then dried so that it is substantially free of water. The treated substrate can be dried by any means known to those skilled in the art. Nonlimiting examples of known drying means include the use of convection ovens, radiant heat sources, microwave ovens, forced air ovens, and heated rollers or cans. Drying also includes air drying without the addition of heat energy, other than that present in the ambient environment. Also, a combination of various drying methods can be used.

Preferably, upon wetting, the articles of the present invention are capable of generating an Average Lather Volume of greater than or equal to about 30 ml, more preferably greater than or equal to about 50 ml, even more preferably greater than or equal to about 75 ml, and most preferably greater than or equal to about 150 ml.

Methods of Cleansing and Conditioning the Skin or Hair

The present invention also relates to a method of cleansing and conditioning the skin or hair with a personal cleansing article of the present invention. These methods comprise the steps of wetting with water a substantially dry, disposable, single use personal cleansing article comprising a water insoluble substrate, a lathering surfactant, and a conditioning component, and contacting the skin or hair with such wetted article. In further embodiments, the present invention is also useful for delivering various active ingredients to the skin or hair.

The articles of the present invention are substantially dry and are intended to be wetted with water prior to use. The article is wetted by immersion in water or by placing it under a stream of water. Lather is generated from the article by mechanically agitating and/or deforming the article either prior to or during contact of the article with the skin or hair. Preferably, upon wetting, the articles of the present invention generate an Average Lather Volume of greater than or equal to about 30 ml, more preferably greater than or equal to about 50 ml, even more preferably greater than or equal to about 75 ml, and most preferably greater than or equal to about 150 ml. The resulting lather is useful for cleansing and conditioning the skin or hair. During the cleansing process and subsequent rinsing with water, the conditioning agents and active ingredients are deposited onto the skin or hair. Deposition of conditioning agents and active ingredients are enhanced by the physical contact of the substrate with the skin or hair.

Method of Consistently Depositing Conditioning Agents and any Active Ingredients onto the Skin or Hair The articles of the present invention are useful for consistently depositing the conditioning agents of the present invention to the skin or hair. In further embodiments where an active ingredient is present, the compositions are also useful for consistently depositing the active ingredient to the skin or hair.

The articles of the present invention have a deposition consistency of greater than about 60%, preferably greater than about 65%, more preferably greater than about 70%, and most preferably greater than about 75%.

The deposition consistency measurement is the quotient obtained from dividing the deposition of conditioning agents via "non-ideal lathering and use" by deposition of conditioning agents via "ideal lathering and use." Non-ideal lathering, as used herein, means that lathering is achieved by rubbing the surface of the article containing the conditioning agents and then contacting the skin or hair with the same surface. This causes inefficient deposition of the conditioning agents because some of the conditioning agents become emulsified by the surfactant. Ideal lathering, as used herein, means that lathering is achieved by rubbing the surface of the article not containing conditioning agents and then contacting the skin or hair with the surface containing the conditioning component. The same reference points would apply if both surfaces of the substrate are treated with the conditioning agents (e.g., deposition obtained from lathering and contacting the skin with the same lathered surface containing emulsified conditioning agents versus contacting the skin with the non-lathered surface which contains non-emulsified conditioning agents). Deposition consistency is maximized when the lipid hardness value of the conditioning component is greater than about 0.02 kg.

Quantification of the conditioning component deposited on the skin or hair can be measured using a variety of standard analytical techniques well known to the chemist of ordinary skill in the art. Such methods include for instance extraction of an area of the skin or hair with a suitable solvent followed by analysis by chromatography (i.e., gas chromatography, liquid chromatography, supercritical fluid chromatography, etc.), IR spectroscopy, UV/VIS spectroscopy, mass spectrometry, etc. Direct measurements can also be made on the skin or hair by techniques such as IR spectroscopy, UV/VIS spectroscopy, opacity measurements, fluoresce spectroscopy, ESCA spectroscopy, and the like.

In a typical method for measuring deposition, a article of the present invention is wetted with water and squeezed and agitated to generate a lather. The article is then rubbed for approximately 15 seconds on a site, approximately about 25 $cm^2$ to about 300 $cm^2$, preferably about 50 $cm^2$ to about 100 $cm^2$, on the skin or head which has been demarcated using an appropriate indelible marker. The site is then rinsed for approximately 10 seconds and then allowed to air dry for approximately 10 minutes. The site is then either extracted and the extracts analyzed, or analyzed directly using any techniques such as those exemplified above.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name, and all weights are in percent actives.

Examples 1–5

I. The Substrate

A multi-layered substrate, as described in FIGS. 1, 2, 3, 4, 5A, and 5B, is prepared as herein described.

II. The Surfactant Phase

In a suitable vessel, mix the following ingredients at room temperature. Add heat as necessary to obtain uniformity.

| | Weight Percent | | | | |
|---|---|---|---|---|---|
| Ingredients | Example 1 | Example 2 | Example 3 | Example 4 | Example 5 |
| Water | QS 100 | QS 100 | QS 100 | QS 100 | QS 100 |
| Polyquaternium-10 | — | 0.25 | — | — | — |
| PEG 14M | — | 0.5 | 0.5 | — | — |
| Hydroxypropyltrimonium Chloride | — | — | — | — | 0.25 |
| Hydroxyelthylcellulose | 0.25 | — | — | — | 0.5 |
| Guar Gum | 0.25 | — | — | — | — |

Add the following components to the mixture of the above components.

| | | | | | |
|---|---|---|---|---|---|
| Disodium EDTA | 0.10 | 0.10 | 0.10 | 0.10 | 0.10 |
| Sodium Lauroyl Sarcosinate | 3.33 | 3.33 | 3.33 | 3.33 | 3.33 |
| Sodium Lauroamphoacetate | — | — | — | — | 3.33 |
| Cocamidopropyl Betaine | 3.33 | 3.33 | 3.33 | 3.33 | — |
| Decyl Polyglucoside | 3.33 | 3.33 | 3.33 | 3.33 | 3.33 |
| Methyl Paraben | 0.25 | 0.25 | 0.25 | 0.25 | 0.25 |
| Phenoxyethanol | 0.3 | 0.3 | 0.3 | 0.3 | 0.3 |
| Benzyl Alcohol | 0.3 | 0.3 | 0.3 | 0.3 | 0.3 |
| Glycerin | — | — | — | — | 3.0 |
| Urea | | | | — | 1.0 |

In a separate mixing vessel add the following components. Mix (with heat to 40° C. as necessary) until propyl paraben is dissolved.

| | | | | | |
|---|---|---|---|---|---|
| Water | 2.0 | 2.0 | 2.0 | 2.0 | 2.0 |
| Butylene Glycol | 2.0 | 2.0 | 2.0 | 2.0 | 2.0 |
| Propyl Paraben | 0.15 | 0.15 | 0.15 | 0.15 | 0.15 |

Add this mixture to the first mixing vessel. Apply 1.5–2.5 g of the resultant mixture to a non-woven substrate and then dry.

III. Optional Lipid Phase
In a suitable vessel, mix the following components with heat until molten (between 75–115° C.).

| | | | | | |
|---|---|---|---|---|---|
| SEFA* Cottonate | 48.00 | 48.00 | 48.00 | 48.00 | 48.00 |
| SEFA* Behenate | 12.00 | — | — | — | — |
| Vitamin E Acetate | — | 2.0 | 2.0 | 2.0 | 2.0 |
| Petrolatum | 10.00 | 10.00 | 10.00 | 10.00 | 23.00 |
| Tribehenin | 5.00 | 5.0 | 5.0 | 5.0 | 5.0 |
| C10–C30 Cholesterol/Lanosterol Esters | 25.00 | 23.00 | 23.00 | 23.00 | 10.00 |
| Synthetic Beeswax | — | 3.0 | 3.0 | 3.0 | — |
| Polyethylene Wax | — | 9.0 | 9.0 | 9.0 | — |
| Paraffin | — | — | — | — | 12.00 |
| Amount added to cloth | 0.25 | 0.25 | 0.35 | 0.10 | 0.25 |

*SEFA is an acronym for sucrose esters of fatty acids

Apply the amount of this phase (shown in the above table) to the substrate already containing the materials from the Surfactant and Water Soluble Conditioner phases. Apply the the lipid phase in a liquid/molten state (e.g., at or above the melting temperature of the resulting lipid mixture) and then cooled. The resulting cleansing article is used by wetting with water and is useful for simultaneously cleansing the skin or hair and depositing the conditioning agents onto the skin or hair in a consistent manner.

In alternative manufacturing procedures, the lathering surfactants, conditioning component, and optional ingredients are separately or simultaneously added onto or impregnated into either or both surfaces of the water insoluble substrate. If the substrate is a laminate the before mentioned components are applied to either or both surfaces of (i) either or both layers prior to combining the layers into a laminate, or (ii) after the layers are combined into a laminate. The process of adding onto or impregnating into the substrate the surfactant and/or conditioning component is achieved by spraying, printing, splashing, dipping, or coating.

In alternative embodiments, other substrates such as woven substrates, hydroentangled substrates, natural sponges, synthetic sponges, or polymeric netted meshes are substituted for the present substrate.

Examples 6–10

I. The Substrate
A multi-layered substrate, as described in FIGS. 1, 2, 3, 4, 5A, and 5B, is prepared as herein described.

II. The Surfactant Phase
In a suitable vessel, mix the following components at room temperature. Add heat as if necessary to obtain uniformity.

| | Weight Percent | | | | |
|---|---|---|---|---|---|
| Ingredients | Example 6 | Example 7 | Example 8 | Example 9 | Example 10 |
| Water | QS 100 | QS 100 | QS 100 | QS 100 | QS 100 |
| Polyquaternium-10 | — | 0.25 | — | — | — |
| PEG 14M | — | 0.5 | 0.5 | — | — |
| Hydroxypropyltrimonium Chloride | — | — | — | — | 0.25 |
| Hydroxyelthylcellulose | 0.25 | — | — | — | 0.5 |
| Guar Gum | 0.25 | — | — | — | — |

Add the following components to the mixture of the above components

| | | | | | |
|---|---|---|---|---|---|
| Disodium EDTA | 0.10 | 0.10 | 0.10 | 0.10 | 0.10 |
| Sodium Lauroyl Sarcosinate | 3.33 | 3.33 | 3.33 | 3.33 | 3.33 |
| Sodium Lauroamphoacetate | — | — | — | — | 3.33 |
| Cocamidopropyl Betaine | 3.33 | 3.33 | 3.33 | 3.33 | — |
| Decyl Polyglucoside | 3.33 | 3.33 | 3.33 | 3.33 | 3.33 |
| Methyl Paraben | 0.25 | 0.25 | 0.25 | 0.25 | 0.25 |
| Phenoxyethanol | 0.3 | 0.3 | 0.3 | 0.3 | 0.3 |
| Benzyl Alcohol | 0.3 | 0.3 | 0.3 | 0.3 | 0.3 |
| Glycerin | — | — | — | — | 3.0 |
| Urea | | | | — | 1.0 |

In a separate mixing vessel, add the following components. Mix (with heat to 40° C. as necessary) until propyl paraben is dissolved.

| | | | | | |
|---|---|---|---|---|---|
| Water | 2.0 | 2.0 | 2.0 | 2.0 | 2.0 |
| Butylene Glycol | 2.0 | 2.0 | 2.0 | 2.0 | 2.0 |
| Propyl Paraben | 0.15 | 0.15 | 0.15 | 0.15 | 0.15 |

Add this mixture to the first mixing vessel. Apply 1.5–2.5 g of the resultant mixture to a non-woven substrate and then dry.

III. Optional Conditioning Emulsion,
In a suitable vessel, the following ingredients are mixed with heat until molten (between 75–115° C.)

| | | | | | |
|---|---|---|---|---|---|
| SEFA* Cottonate | 27.36 | 27.36 | 27.36 | 27.36 | 27.36 |
| SEFA* Behenate | 6.84 | — | — | 6.84 | — |
| Polyethylene Wax | — | 5.13 | 6.84 | — | — |
| Synthetic Beeswax | — | 1.71 | — | — | — |
| Petrolatum | 5.7 | 5.7 | 5.7 | 5.7 | 13.1 |
| C10–C30 cholesterol/lanosterol esters | 13.1 | 13.1 | 13.1 | 13.1 | 5.7 |
| Vitamin E Acetate | 1.14 | 1.14 | 1.14 | 1.14 | 1.14 |
| Tribehenin | 2.85 | 2.85 | 2.85 | 2.85 | 2.85 |
| Decaglyceryl Dipalmitate | 0.3 | — | 0.3 | 0.3 | — |
| Triglyceryl Monostearate | 2.7 | 0.3 | 2.7 | 2.7 | 0.3 |
| Decaglyceryl Stearate | — | 2.7 | — | — | 2.7 |
| Polyglyceryl Tristearate | — | — | — | — | — |

*SEFA is an acronym for sucrose esters of fatty acids

Mix the following components together at room temperature until homogeneous. Once the mixture above is completely melted, stop heating and slowly add the following components while continuing to mix:

| | | | | | |
|---|---|---|---|---|---|
| Water | — | — | 5.0 | 6.0 | 5.0 |
| Glycerin | 35.0 | 30.0 | 25.0 | 25.0 | 21.0 |
| Dex Panthenol | — | 5.0 | 3.0 | 2.0 | 2.0 |
| Urea | — | 1.0 | — | 2.0 | 1.0 |
| PEG-30 | — | 4.0 | 2.0 | 2.0 | 5.0 |
| Propylene glycol | — | — | 4.0 | 3.0 | 5.75 |
| Polyquaternium-10 | — | — | 1.0 | — | 0.25 |

Apply 0.1–1.0 g of this phase in a liquid/molten state to the substrate already containing the materials from the Surfactant Phase. Cool to room temperature (about 20° C.) after application. The resulting cleansing and conditioning article is used by wetting with water and is useful for cleansing the skin or hair and for depositing the conditioning emulsions onto the skin or hair.

In alternative manufacturing procedures, the lathering surfactants, conditioning emulsions, and optional ingredients are separately or simultaneously added onto or impregnated into either surface of (i) either or both layers prior to combining the layers into a laminate, or (ii) after the layers are combined into a laminate. The process of adding onto or impregnating into the substrate the surfactant and/or conditioning component is achieved by spraying, printing, splashing, dipping, or coating.

Similarly, the lathering surfactant and the conditioning emulsion can be added to the substrate in any order. Non-limiting examples of the process sequences include (i) first adding surfactant to the second layer, then joining the substrate, then treating with the conditioning component; (ii) first combining surfactant with conditioning component then treating the second layer, then joining the two layers; (iii) prior to joining the two layers, treating the second layer with the surfactant first and then the conditioning component second, then joining the two layers.

In alternative embodiments, other substrates such as woven substrates, hydroentangled substrates, natural sponges, synthetic sponges, or polymeric netted meshes are substituted for the present substrate.

What is claimed is:

1. A disposable, single use personal care cleansing and conditioning article comprising:
   (A) a water insoluble substrate, wherein at least a first portion of said substrate is wet extensible and at least a second portion of said substrate is less wet extensible than said first portion, wherein selected portions of said first portion are joined to said second portion in a manner which is sufficient to inhibit wet extension of said first portion in the plane of said first portion, and wherein said selected portions of said first portion are bonded to said second portion to provide a continuous bonded region which defines a plurality of discrete unbonded regions; and
   (B) at least one lathering surfactant added onto or impregnated into said substrate, wherein said article is substantially dry prior to use.

2. An article according to claim 1 wherein said lathering surfactant comprises from about 0.5% to about 12.5% by weight of said water insoluble substrate.

3. An article according to claim 2 wherein said lathering surfactant is selected from the group consisting of anionic lathering surfactants, nonionic lathering surfactants, amphoteric lathering surfactants, and mixtures thereof.

4. An article according to claim 3 wherein said anionic lathering surfactant is selected from the group consisting of sarcosinates, sulfates, isethionates, phosphates, taurates, lactylates, glutamates and mixtures thereof; wherein said nonionic lathering surfactant is selected from the group consisting of amine oxides, alkyl glucosides, alkyl polyglucosides, polyhydroxy fatty acid amides, alkoxylated fatty acid esters, sucrose esters, and mixtures thereof; and wherein said amphoteric lathering surfactant is selected from the group consisting of betaines, sultaines, hydroxysultaines, alkyliminoacetates, iminodialkanoates, aminoalkanoates, and mixtures thereof.

5. An article according to claim 2 further comprising a conditioning component added onto or impregnated into said substrate.

6. An article according to claim 5 wherein said conditioning component comprises from about 0.05% to about 99% by weight of said water insoluble substrate, and wherein said conditioning component has a lipid hardness value of greater than about 0.02 kg.

7. An article according to claim 6 wherein said conditioning component comprises at least one oil soluble conditioning agent and at least one lipid hardening material such that the weighted arithmetic mean solubility parameter of said oil soluble conditioning agent is less than or equal to 10.5, and wherein said lipid hardness value of the conditioning component is greater than about 0.05 kg.

8. An article according to claim 6 wherein said lipid hardness value of the conditioning component is greater than about 0.05 kg, and wherein said conditioning component comprises at least one material selected from the group consisting of fatty acids, esters of fatty acids, fatty alcohols, ethoxylated alcohols, polyol polyesters, glycerin monoesters, glycerin polyesters, epidermal and sebaceous hydrocarbons, lanolin, straight and branched hydrocarbons, silicone oil, silicone gum, vegetable oil, vegetable oil adduct, hydrogenated vegetable oils, nonionic polymers, natural waxes, synthetic waxes, polyolefinic glycols, polyolefinic monoester, polyolefinic polyesters, cholesterols, cholesterol esters and mixtures thereof.

9. An article according to claim 8 wherein said conditioning component comprises at least one material selected from the group consisting of $C_7$–$C_{40}$ straight and branched chain hydrocarbons, C1–C30 monoesters and polyesters of sugars, polyol polyesters, C1–C30 fatty acids, C1–C30 fatty alcohols, C1–C30 ethoxylated alcohols, glycerin mono and tri-esters, cholesterols, cholesterol esters natural waxes, synthetic waxes and mixtures thereof.

10. An article according to claim 9 wherein said conditioning component comprises at least one material selected from the group consisting of paraffin, mineral oil, petrolatum, cholesterols, cholesterol esters, stearyl alcohol, cetyl alchohol, cetearyl alcohol, behenyl alcohol, C10-30 polyesters of sucrose, stearic acid, palmitic acid, behenic acid, oleic acid, linoleic acid, myristic acid, lauric acid, ricinoleic acid, steareth-1-100, cetereath 1–100, cholesterols, cholesterol esters, glyceryl tribehenate, glyceryl dipalmitate, glyceryl monostearate, trihydroxystearin, ozokerite wax, jojoba wax, lanolin wax, ethylene glycol distearate, candelilla wax, carnauba wax, beeswax, silicone waxes.

11. An article according to claim 5 wherein said conditioning component is a conditioning emulsion comprising,
   (A) an internal phase comprising a water soluble conditioning agent selected from one or more water soluble agents such that the weighted arithmetic mean solubility parameter of said water soluble conditioning agent is greater than 10.5, and
   (B) an external phase comprising at least one oil soluble conditioning agent and at least one lipid hardening material selected such that the weighted arithmetic mean solubility parameter of said water soluble conditioning agent is greater than 10.5.

12. An article according to claim 2 wherein said cleansing article further comprises a safe and effective amount of one or more active ingredients selected from the group consisting of anti-acne actives, anti-wrinkle and anti-skin atrophy actives skin barrier repair actives, non-steroidal cosmetic soothing actives, non-stearoidal anti-inflammatory actives, topical anesthetics, artificial tanning agents and accelerators, skin lightening actives, sebum stimulators, sebum inhibitors, anti-microbial and anti-fungal agents, sunscreen actives, anti-oxidants, and mixtures thereof.

13. An article according to claim 12 wherein said active ingredient is selected from the group consisting of salicylic acid, benzoyl peroxide, 3-hydroxy benzoic acid, glycolic acid, lactic acid, 4-hydroxy benzoic acid, acetyl salicylic acid, niacinamide, cis-retinoic acid, trans-retinoic acid, retinol, retinyl palmitate, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, 2-ethylhexyl p-methoxycinnamic acid, oxybenzone, 2-phenylbenzimidozole-5-sulfonic acid, dihydroxyacetone, panthenol, lactic acid, arbutin, kojic acid, allantoin, cholesterol, $C_{10}$–$C_{30}$ cholesterol/lanosterol esters, tocopherol, tocopheryl acetate, and mixtures thereof.

14. An article according to claim 6 wherein said water insoluble substrate comprises:
   (A) a first layer, the first layer being wet extensible in the plane of the first layer when the first layer is wetted; and
   (B) a second layer which is less wet extensible when wetted than is said first layer;
   wherein selected portions of said first layer are joined to said second layer in a manner which is sufficient to inhibit wet extension of said first layer in the plane of said first layer.

15. The article of claim 14 wherein said first layer has a wet extensibility of at least about 4 percent.

16. The article of claim 15 wherein said first layer has a wet extensibility of at least about 10 percent.

17. The article of claim 15 wherein said first layer comprises a creped paper web and said second layer comprises a nonwoven web.

18. An article according to claim 17 wherein at last one portion of said water insoluble substrate is apertured.

19. The article of claim 18 wherein selected portions of said first substrate layer are adhesively bonded to said second substrate layer to provide a plurality of generally parallel, spaced apart bonded regions and a plurality of generally parallel, spaced apart unbonded regions within said substrate.

20. The article of claim 19 wherein selected portions of said first substrate layer are adhesively bonded to said second substrate layer to provide a continuous network bonded region which defines a plurality of discrete unbonded regions.

21. The article of claim 14 having a wet to dry caliper ratio greater than 1.0.

22. The article of claim 1 wherein the article is capable of generating an Average Lather Volume of greater than or equal to about 30 ml upon wetting.

23. A method of manufacturing a disposable, single use personal care cleansing and conditioning article comprising the step of separately or simultaneously adding onto or impregnating into a water insoluble substrate, wherein at least a first portion of said substrate is wet extensible and at least a second portion of said substrate is less wet extensible than said first portion,
   (A) at least one lathering surfactant, and
   (B) a conditioning component having a lipid hardness value of greater than about 0.02 kg,
wherein said resulting article is substantially dry.

24. The method of claim 23 wherein the article is capable of generating an Average Lather Volume of greater than or equal to about 30 ml upon wetting.

25. A method of cleansing and conditioning the skin or hair with a personal cleansing article, comprising the steps of:
   (A) wetting with water a substantially dry, disposable, single use personal cleansing article comprising:
      (i) a water insoluble substrate, wherein at least a first portion of said substrate is wet extensible and at least a second portion of said substrate is less wet extensible than said first portion,
      (ii) at least one lathering surfactant, and
      (iii) a conditioning component having a lipid hardness value of greater than about 0.02 kg, and
   (B) contacting the skin or hair with said wetted article.

26. The method of claim 25 wherein the article is capable of generating an Average lather Volume of greater than or equal to about 30 ml upon wetting.

27. A method according to claim 23 wherein the conditioning agents of said conditioning component are delivered to the skin or hair with a deposition consistency of at least about 60%.

* * * * *

UNITED STATES PATENT AND TRADEMARK OFFICE
CERTIFICATE OF CORRECTION

PATENT NO. : 6,153,208
DATED : November 28, 2000
INVENTOR(S) : McAtee et al.

It is certified that error appears in the above-identified patent and that said Letters Patent is hereby corrected as shown below:

Column 11,
Line 49, "111382-01" should read -- H1382-01 --.

Column 15,
Line 14, "Keybak851V" should read -- Kebak® 951V --.
Line 25, "1100%" should read -- 100% --.

Column 16,
Line 11, a gravure" should read -- gravure --.
Line 55, "111382-01" should read -- H1382-01 --.

Column 17,
Line 39, "vertical y" should read -- vertically --.
Line 41, "ex tension" should read -- extension --.
Line 45, "re moving" should read -- removing --.

Column 18,
Line 3, "the n" should read -- then --.
Line 5, "hanging 30" should read -- hanging --.
Line 22, "≥" should read -- $\geq$ --.

Column 21,
Lines 32-33, "dimethylbexadecylamine" should read -- dimethylhexadecylamine --.

Column 27,
Line 10, after the word "and" please insert -- arachidate in a 1:2 molar ratio; the octaester of raffinose in which the --.
Line 67, "SiR2011" should read -- SiR20H --.

Column 31,
Line 53, DFISI00" should read -- DFIS100 --.

UNITED STATES PATENT AND TRADEMARK OFFICE
CERTIFICATE OF CORRECTION

PATENT NO.    : 6,153,208
DATED         : November 28, 2000
INVENTOR(S)   : McAtee et al.

It is certified that error appears in the above-identified patent and that said Letters Patent is hereby corrected as shown below:

Column 34,
Line 8, "Tumey" should read -- Turney --;
Line 58, "thereof," should read -- thereof; --.

Column 37,
Line 21, "LKFN" should read -- LKTN --.
Line 43, "Jaguare" should read -- Jaguar --.
Line 49, Polyquatemium" should read -- Polyquaternium --.

Column 39,
Lines 37, 39, 42 and 51, "quatemized" should read -- quaternized --.

Column 40,
Line 3, "Polyquatemium-16" should read -- Polyquarternium-16 --.
Line 16, "Polyquatemium 6" should read -- Polyquarternium 6 --.
Line 16, "Polyquatemium 7" should read -- Polyquarternium 7 --.
Line 26, "Quatemium-40" should read -- Quaternium-40 --.

Column 42,
Line 67, "dehydrodicugenol" should read -- dehydrodieugenol --.

Column 43,
Lines 27-28, "cystcamine" should read -- cysteamine --.
Line 33, "linolcate;" should read -- linoleate; --.

Column 44,
Line 27, aesc in," should read -- aescin, --.
Line 66, "urimel" should read -- urimei --.

Column 45,
Line 35, after the word "or", omit the word -- an --.
Line 35, after the word "or" insert the word -- provide --.

UNITED STATES PATENT AND TRADEMARK OFFICE
CERTIFICATE OF CORRECTION

PATENT NO. : 6,153,208
DATED : November 28, 2000
INVENTOR(S) : McAtee et al.

It is certified that error appears in the above-identified patent and that said Letters Patent is hereby corrected as shown below:

Column 47,
Line 17, "PILANSERVATIVE" should read -- PLANSERVATIVE --.

Column 58,
Line 48, "lather" should read -- Lather --.

Signed and Sealed this

Twenty-fourth Day of August, 2004

JON W. DUDAS
*Director of the United States Patent and Trademark Office*